(12) United States Patent
Komori

(10) Patent No.: US 7,714,168 B2
(45) Date of Patent: May 11, 2010

(54) AMIDE COMPOUNDS AND THEIR USE

(75) Inventor: Takashi Komori, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/084,129

(22) PCT Filed: Oct. 20, 2006

(86) PCT No.: PCT/JP2006/321449

§ 371 (c)(1),
(2), (4) Date: Aug. 6, 2008

(87) PCT Pub. No.: WO2007/049729

PCT Pub. Date: May 3, 2007

(65) Prior Publication Data

US 2008/0319080 A1  Dec. 25, 2008

(30) Foreign Application Priority Data

Oct. 27, 2005  (JP) .............................. 2005-312427

(51) Int. Cl.
*C07C 233/65* (2006.01)
*A01N 37/18* (2006.01)

(52) U.S. Cl. .................. 564/176; 564/74; 514/599; 514/622

(58) Field of Classification Search ............ 564/74, 564/176; 514/599, 622
See application file for complete search history.

(56) References Cited

U.S. PATENT DOCUMENTS 4,946,865 A  8/1990  Takahashi et al.

FOREIGN PATENT DOCUMENTS

| EP | 0 230 773 | 8/1987 |
|---|---|---|
| GB | 1 539 007 | 1/1979 |

OTHER PUBLICATIONS

International Search Report issued Apr. 11, 2007 in the International (PCT) Application PCT/JP2006/321449 of which the present application is the U.S. National Stage.

Itaru Watanabe et al., "Specific Inhibition of RNA Replicase by Certain Chemical Compounds", Proceedings of the Japan Academy, 1038-1043 CODEN: PJACAW: ISSN: 0021-4280, vol. 44, No. 10, pp. 1038-1043, XP009078315, 1968.

Esther Y. Chao et al., "A Novel Method for the Generation of Nitrile Oxides on Solid Phase: Application to the Synthesis of Substituted Benzopyranoisoxazoles", Organic Letters, vol. 4, No. 3, pp. 323-326, XP002418099, 2002.

*Primary Examiner*—Shailendra Kumar
(74) *Attorney, Agent, or Firm*—Wenderoth, Lind & Ponack, L.L.P.

(57) ABSTRACT

Since an amide compound represented by the formula (1)

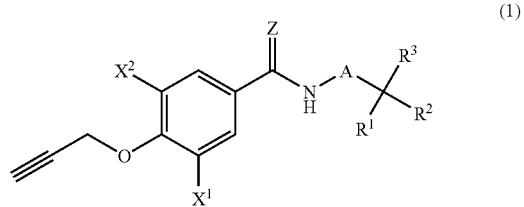

is effective for controlling plant diseases, it is useful as an effective ingredient of a composition for controlling plant diseases.

12 Claims, No Drawings

AMIDE COMPOUNDS AND THEIR USE

This application is a 371 of PCT/JP2006/321449, filed Oct. 20, 2006.

TECHNICAL FIELD

The present invention relates to amide compounds and their use.

BACKGROUND ART

Heretofore, the development of compositions for controlling plant diseases has been carried out and many compounds which are effective for controlling plant diseases have been found. However, their activity is not always sufficient. Accordingly, there are further demands for developing novel compounds having plant disease-controlling activity.

DISCLOSURE OF THE INVENTION

The present invention is intended to provide a compound having superior plant disease-controlling activity.

The present inventor has intensively studied in order to find a compound having superior plant disease-controlling activity and, as a result, has found that an amide compound represented by the formula (I) has superior plant disease-controlling activity. Thus, the present invention has been completed.

That is, the present invention provides:

[1] An amide compound represented by the formula (1)

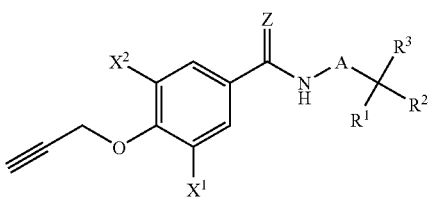

(1)

wherein $X^1$ represents a fluorine atom or a methoxy group, $X^2$ represents a hydrogen atom, a fluorine atom or a methoxy group, Z represents an oxygen atom or a sulfur atom, A represents a single bond or a methylene group, $R^1$ and $R^2$ represent independently a C1 to C4 alkyl group, and $R^3$ represents a hydrogen atom, a C1 to C4 alkyl group, a C2 to C4 alkenyl group, a C2 to C4 alkynyl group, a cyano group, a carboxyl group, or a (C1 to C3 alkoxy)carbonyl group;

[2] The amide compound according to the above [1], wherein, in the formula (1), Z is an oxygen atom;

[3] The amide compound according to the above [1] or [2], wherein, in the formula (1), $X^1$ is a fluorine atom and $X^1$ is a hydrogen atom; or $X^1$ is a fluorine atom and $X^2$ is a fluorine atom; or $X^1$ is a methoxy group and $X^2$ is a hydrogen atom; or $X^1$ is a methoxy group and $X^2$ is a methoxy group;

[4] The amide compound according to the above [1] or [2], wherein, in the formula (1), $X^1$ is a methoxy group and $X^2$ is a methoxy group;

[5] The amide compound according to the above [1] or [2], wherein, in the formula (1), $X^1$ is a methoxy group and $X^2$ is a hydrogen atom;

[6] The amide compound according to any one of the above [1] to [5], wherein, in the formula (1), A is a single bond;

[7] The amide compound according to any one of the above [1] to [6], wherein, in the formula (1), $R^1$ is a methyl group or an ethyl group and $R^2$ is a methyl group, an ethyl group, a 1-methylethyl group, a 1,1-dimethylethyl group or a 1-methylpropyl group;

[8] The amide compound according to any one of the above [1] to [7], wherein, in the formula (1), $R^3$ is a hydrogen atom or a methyl group;

[9] The amide compound according to the above [1] or [2], wherein, in the formula (1), $X^1$ is a fluorine atom and $X^2$ is a hydrogen atom;

[10] The amide compound according to the above [1] or [2], wherein, in the formula (1), $X^1$ is a fluorine atom and $X^2$ is a fluorine atom;

[11] A composition for controlling plant diseases which comprises the amide compound according to any one of the above [1] to [10] as an effective ingredient and an inactive carrier;

[12] A method for controlling plant diseases which comprises a step of treating a plant or soil growing the plant with an effective amount of the amide compound according to any one of the above [1] to [10]; and

[13] Use of the amide compound according to the above [1] for controlling plant diseases.

Examples of the C1 to C4 alkyl group represented by $R^1$ include a methyl group, an ethyl group, a 1-methylethyl group, a 1,1-dimethylethyl group, a propyl group and a 1-methylpropyl group.

Examples of the C1 to C4 alkyl group represented by $R^2$ include a methyl group, an ethyl group, a 1-methylethyl group, a 1,1-dimethylethyl group, a propyl group and a 1-methylpropyl group.

Examples of the C1 to C4 alkyl group represented by $R^3$ include a methyl group, an ethyl group, a 1-methylethyl group, a 1,1-dimethylethyl group, a propyl group and a 1-methylpropyl group.

Examples of the C2 to C4 alkenyl group represented by $R^3$ include a vinyl group, a 1-propenyl group, a 2-propenyl group, a 2-butenyl group and a 3-butenyl group.

Examples of the C2 to C4 alkynyl group represented by $R^3$ include an ethynyl group, a 1-propynyl group, a 2-propynyl group and a 3-butynyl group.

The (C1 to C3 alkoxy)carbonyl group represented by $R^3$ includes a methoxycarbonyl group and an ethoxycarbonyl group.

A group represented by the formula:

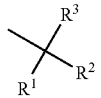

is a secondary or tertiary alkyl group and specific examples thereof include a 1-methylethyl group, a 1-methylpropyl group, a 1-methylbutyl group, a 1-ethylpropyl group, a 1,1-dimethylethyl group, a 1,1-dimethylpropyl group, a 1,2-dimethylpropyl group, a 1,2-dimethylbutyl group, a 1,1,2-trimethylpropyl group, a 1,2,2-trimethylpropyl group, a 1,1,2,2-tetramethylpropyl group and a 1-cyano-1,2-dimethylpropyl group.

As an aspect of the present invention, among the compounds of the present invention, for example, the following compounds are mentioned:

The amide compound represented by the formula (1), wherein Z is an oxygen atom;

The amide compound represented by the formula (1), wherein $X^1$ is a fluorine atom and $X^2$ is a hydrogen atom;

The amide compound represented by the formula (1), wherein $X^1$ is a fluorine atom and $X^2$ is a fluorine atom;

The amide compound represented by the formula (1), wherein $X^1$ is a methoxy group and $X^2$ is a methoxy group;

The amide compound represented by the formula (1), wherein $X^1$ is a methoxy group and $X^2$ is a hydrogen atom;

The amide compound represented by the formula (1), wherein A is a single bond;

The amide compound represented by the formula (1), wherein A is a methylene group;

The amide compound represented by the formula (1), wherein $R^1$ is a methyl group or an ethyl group and $R^2$ is a methyl group, an ethyl group, a 1-methylethyl group, a 1,1-dimethylethyl group or a 1-methylpropyl group;

The amide compound represented by the formula (1), wherein $R^3$ is a hydrogen atom or a methyl group;

The amide compound represented by the formula (1), wherein Z is an oxygen atom and A is a single bond;

The amide compound represented by the formula (1), wherein Z is an oxygen atom and A is a methylene group;

The amide compound represented by the formula (1), wherein Z is an oxygen atom, A is a single bond and $R^3$ is a hydrogen atom or a methyl group;

The amide compound represented by the formula (1), wherein Z is an oxygen atom, A is a methylene group, $R^3$ is a hydrogen atom or a methyl group;

The amide compound represented by the formula (1), wherein Z is an oxygen atom, A is a single bond, $R^1$ is a methyl group or an ethyl group, $R^2$ is a methyl group, an ethyl group, a 1-methylethyl group, a 1,1-dimethylethyl group or a 1-methylpropyl group and $R^3$ is a hydrogen atom or a methyl group;

The amide compound represented by the formula (1), wherein Z is an oxygen atom, A is a methylene group, $R^1$ is a methyl group or an ethyl group, $R^2$ is a methyl group, an ethyl group, a 1-methylethyl group, a 1,1-dimethylethyl group or a 1-methylpropyl group and $R^3$ is a hydrogen atom or a methyl group;

The amide compound represented by the formula (1), wherein A is a methylene group, $R^1$ is a methyl group and $R^2$ is a methyl group;

The amide compound represented by the formula (1), wherein A is a methylene group, $R^1$ is a methyl group, $R^2$ is a methyl group and $R^3$ is a hydrogen atom or a C1 to C4 alkyl group;

The amide compound represented by the formula (1), A is a methylene group, $R^1$ is a methyl group, $R^2$ is a methyl group and $R^3$ is a hydrogen atom or a methyl group;

The amide compound represented by the formula (1), A is a single bond, $R^1$ is a methyl group, $R^2$ is a methyl group and $R^3$ is a C1 to C4 alkyl group;

The amide compound represented by the formula (1), wherein A is a single bond, $R^1$ is a methyl group, $R^2$ is a C1 to C4 alkyl group and $R^3$ is a hydrogen atom;

The amide compound represented by the formula (1), wherein A is a single bond, $R^1$ is a methyl group, $R^2$ is a C3 to C4 alkyl group and $R^3$ is a hydrogen atom; and The amide compound represented by the formula (1), wherein A is a single bond, $R^1$ is a methyl group, $R^2$ is a 1-methylethyl group or 1,1-dimethylethyl group and $R^3$ is a hydrogen atom.

Hereinafter, the production process of the compound of the present invention will be illustrated.

The compound of the present invention can be produced by, for example, Production Process 1 to Production Process 6.

Production Process 1

Among the compounds of the present invention, a compound represented by the formula (5) in which Z is an oxygen atom can be produced by reacting a compound represented by the formula (2) with a compound represented by the formula (3) using a dehydration condensation agent.

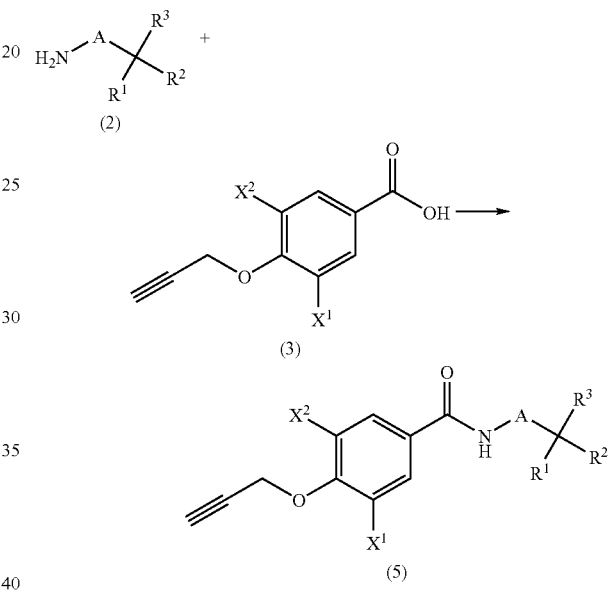

wherein $X^1$ represents a fluorine atom or a methoxy group, $X^2$ represents a hydrogen atom, a fluorine atom or a methoxy group, A represents a single bond or a methylene group, $R^1$ and $R^2$ represent independently a C1 to C4 alkyl group, and $R^3$ represents a hydrogen atom, a C1 to C4 alkyl group, a C2 to C4 alkenyl group, a C2 to C4 alkynyl group, a cyano group, a carboxyl group, or a (C1 to C3 alkoxy)carbonyl group.

The reaction is usually carried out in the presence of a solvent.

Examples of the solvent used for the reaction include ethers such as tetrahydrofuran (hereinafter, occasionally described as THF), ethyleneglycol dimethyl ether, tert-butyl methyl ether (hereinafter, occasionally described as MTBE), etc.; aliphatic hydrocarbons such as hexane, heptane, octane, etc.; aromatic hydrocarbons such as toluene, xylene, etc.; halogenated hydrocarbons such as chlorobenzene, etc.; esters such as butyl acetate, ethyl acetate, etc.; nitriles such as acetonitrile, etc.; acid amides such as N,N-dimethylformamide (hereinafter, occasionally described as DMF), etc.; sulfoxides such as dimethylsulfoxide (hereinafter, occasionally described as DMSO), etc.; and a mixture thereof.

The dehydration condensation agent used for the reaction includes carbodiimides such as 1-ethyl-3-(3-dimethylaminopropyl)carbodiimide hydrochloride (hereinafter, described as WSC), 1,3-dicyclohexylcarbodiimide, etc.

Usually, the compound represented by the formula (3) is used at a proportion of 1 to 3 mol and the dehydration condensation agent is used at a proportion of 1 to 5 mol based on 1 mol of the compound represented by the formula (2).

The reaction temperature is usually in a range of 0 to 140° C. and the reaction time is usually in a range of 1 to 24 hours.

After completion of the reaction, the compound represented by the formula (5) can be isolated by subjecting to post treatment such as filtering a reaction mixture, then extracting the filtrate with an organic solvent, and drying and concentrating organic layer. The isolated compound represented by the formula (5) can also be further purified by chromatography, recrystallization, and the like.

Production Process 2

Among the compounds of the present invention, the compound represented by the formula (5) in which Z is an oxygen atom can be produced by reacting the compound represented by the formula (2) with a compound represented by the formula (4) in the presence of a base.

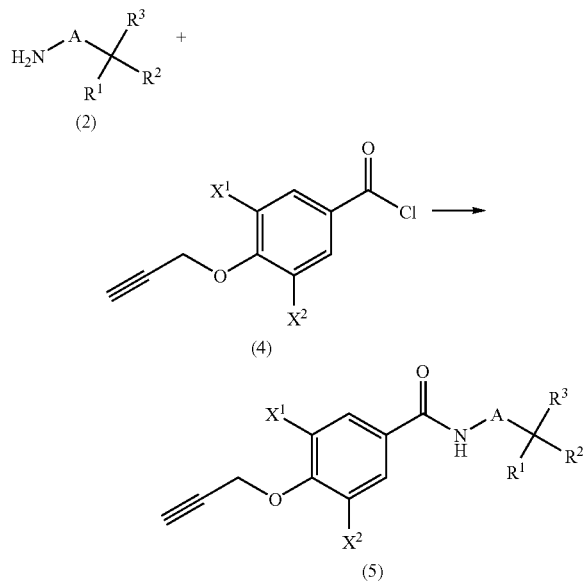

wherein A, $R^1$, $R^2 R^3$, $X^1$ and $X^2$ are as defined above.

The reaction is usually carried out in the presence of a solvent.

Examples of the solvent used for the reaction include ethers such as THF, ethyleneglycol dimethyl ether, MTBE, etc.; aliphatic hydrocarbons such as hexane, heptane, octane, etc.; aromatic hydrocarbons such as toluene, xylene, etc.; halogenated hydrocarbons such as chlorobenzene. etc.; esters such as butyl acetate, ethyl acetate, etc.; nitrites such as acetonitrile, etc.; acid amides such as DMF, etc.; sulfoxides such as DMSO, etc.; and a mixture thereof.

The base used for the reaction includes alkali metal carbonates such as sodium carbonate, potassium carbonate, etc.; tertiary amines such as triethylamine, diisopropylethylamine, etc.; nitrogen-containing aromatic compounds such as pyridine, 4-dimethylaminopyridine, etc.; and the like.

Usually, the compound represented by the formula (4) is used at a proportion of 1 to 3 mol and the base is used at a proportion of 1 to 10 mol based on 1 mol of the compound represented by the formula (2).

The reaction temperature is usually in a range of −20 to 100° C. and the reaction time is usually in a range of 0.1 to 24 hours.

After completion of the reaction, the compound represented by the formula (5) can be isolated by subjecting to post treatment such as extracting a reaction mixture with an organic solvent and drying and concentrating the organic layer. The isolated compound represented by the formula (5) can also be further purified by chromatography, recrystallization, and the like.

Production Process 3

Among the compounds of the present invention, a compound represented by the formula (6) in which Z is a sulfur atom can be produced by reacting the compound represented by the formula (5) in which Z is an oxygen atom with 2,4-bis(4-methoxyphenyl)-1,3-dithia-2,4-diphosphetane-2,4-disulfide (hereinafter, described as Lawesson's Reagent)

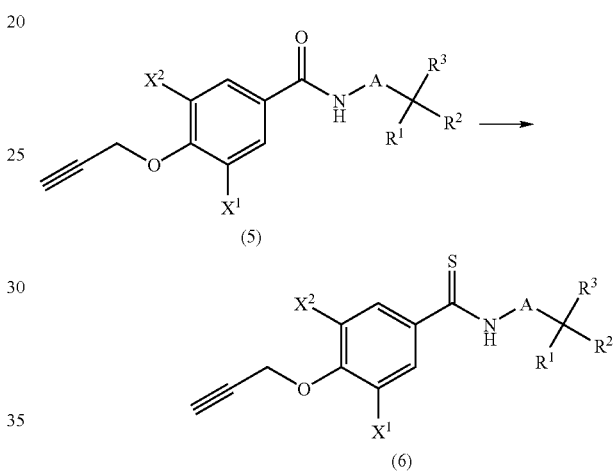

wherein A, $R^1$, $R^2$, $R^3$, $X^1$ and $X^2$ are as defined above.

The reaction is usually carried out in the presence of a solvent.

Examples of the solvent used for the reaction include ethers such as THF, ethyleneglycol dimethyl ether, MTBE, etc.; aliphatic hydrocarbons such as hexane, heptane, octane, etc.; aromatic hydrocarbons such as toluene, xylene, etc.; halogenated hydrocarbons such as chlorobenzene, etc.; organic nitrites such as acetonitrile, butyronitrile, etc.; sulfoxides such as dimethylsulfoxide, etc.; and a mixture thereof.

Usually, the Lawesson's Reagent is used at a proportion of 1 to 2 mol based on 1 mol of the compound represented by the formula (5).

The reaction temperature is usually a range of 25 to 150° C. and the reaction time is usually a range of 0.1 to 24 hours.

After completion of the reaction, the compound represented by the formula (6) can be isolated by subjecting to post treatment such as extracting a reaction mixture with an organic solvent and drying and concentrating the organic layer. The isolated compound represented by the formula (6) can also be further purified by chromatography, recrystallization, and the like.

Production Process 4

Among the compounds of the present invention, a compound represented by the formula (8) in which $X^1$ and $X^2$ are fluorine atoms can be produced according to the following scheme.

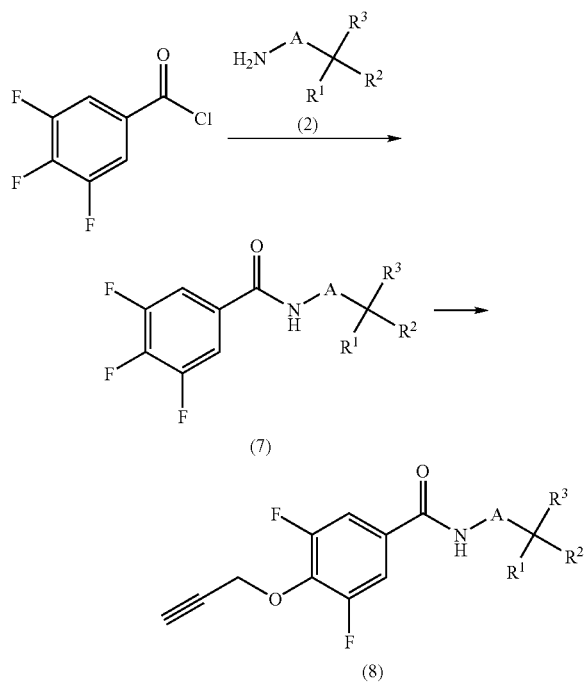

wherein A, $R^1$, $R^2$ and $R^3$ are as defined above.

The compound represented by the formula (7) can be produced by reacting 3,4,5-trifluorobenzoyl chloride with the compound represented by the formula (2) in the presence of a base.

The reaction is usually carried out in the presence of a solvent.

Example of the solvent used for the reaction include ethers such as THF, ethyleneglycol dimethyl ether, MTBE, etc.; aliphatic hydrocarbons such as hexane, heptane, octane, etc.; aromatic hydrocarbons such as toluene, xylene, etc.; halogenated hydrocarbons such as chlorobenzene, etc.; esters such as butyl acetate, ethyl acetate, etc.; nitrites such as acetonitrile, etc.; acid amides such as DMF, etc.; sulfoxides such as dimethylsulfoxide, etc.; and a mixture thereof.

The base used for the reaction includes alkali metal carbonates such as sodium carbonate, potassium carbonate, etc.; tertiary amines such as triethylamine, diisopropylethylamine, etc.; and nitrogen-containing aromatic compounds such as pyridine, 4-dimethylaminopyridine, etc.; and the like.

Usually, 3,4,5-trifluorobenzoyl chloride is used at a proportion of 1 to 3 mol and the base is used at a proportion of 1 to 10 mol based on 1 mol of the compound represented by the formula (2).

The reaction temperature is usually in a range of −20 to 100° C. and the reaction time is usually in a range of 0.1 to 24 hours.

After completion of the reaction, the compound represented by the formula (7) can be isolated by subjecting to post treatment such as extracting a reaction mixture with an organic solvent and drying and concentrating the organic layer. The isolated compound represented by the formula (7) can also be further purified by chromatography, recrystallization and the like.

The compound represented by the formula (8) can be produced by reacting the compound represented by the formula (7) with propargyl alcohol in the presence of a base.

The reaction is usually carried out in the presence of a solvent.

Examples of the solvent used for the reaction include ethers such as THF, ethyleneglycol dimethyl ether, MTBE, etc.; aliphatic hydrocarbons such as hexane, heptane, octane, etc.; ketones such as acetone, methyl ethyl ketone, methyl isobutyl ketone, etc.; aromatic hydrocarbons such as toluene, xylene, etc.; halogenated hydrocarbons such as chlorobenzene, etc.; esters such as butyl acetate, ethyl acetate, etc.; nitrites such as acetonitrile, etc.; acid amides such as DMF, etc.; sulfoxides such as dimethylsulfoxide, etc.; and a mixture thereof.

The base used for the reaction includes alkali metal carbonates such as sodium carbonate, potassium carbonate, etc.; alkali metal bicarbonates such as sodium bicarbonate, etc.; alkali metal hydrides such as sodium hydride, etc.; alkali metal hydroxides such as sodium hydroxide, etc.; and the like.

Usually, propargyl alcohol is used at a proportion of 1 to 3 mol and the base is used at a proportion of 1 to 2 mol based on 1 mol of the compound represented by the formula (7).

The reaction temperature is usually in a range of −20 to 100° C. and the reaction time is usually in a range of 0.1 to 24 hours.

After completion of the reaction, the compound represented by the formula (8) can be isolated by subjecting to post treatment such as extracting a reaction mixture with an organic solvent and drying and concentrating the organic layer. The isolated compound represented by the formula (8) can also be further purified by chromatography, recrystallization, and the like.

Production Process 5

Among the compounds of the present invention, the compound represented by the formula (5) in which Z is an oxygen atom can be produced by reacting a compound represented by the formula (9) with propargyl bromide in the presence of a base.

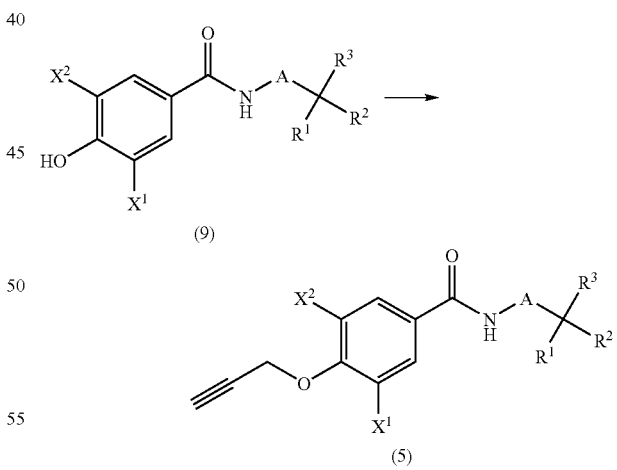

wherein A, $R^1$, $R^2$, $R^3$, $X^1$ and $X^2$ are as defined above.

The reaction is usually carried out in the presence of a solvent.

Examples of the solvent used for the reaction include ethers such as THF, ethyleneglycol dimethyl ether, MTBE, etc.; aromatic hydrocarbons such as toluene, xylene, etc.; halogenated hydrocarbons such as chlorobenzene, etc.; nitrites such as acetonitrile, etc.; acid amides such as DMF, etc.; sulfoxides such as dimethylsulfoxide, etc.; ketones such as acetone, methyl ethyl ketone, methyl isobutyl ketone, etc.; water; and a mixture thereof.

The base used for the reaction includes alkali metal carbonates such as sodium carbonate, potassium carbonate, cesium carbonate, etc.; alkali metal hydroxides such as sodium hydroxide, etc.; alkali metal hydrides such as sodium hydride, etc.; and the like.

Usually, propargyl bromide is used at a proportion of 1 to 3 mol and the base is used at a proportion of 1 to 3 mol based on 1 mol of the compound represented by the formula (9).

The reaction temperature is usually in a range of −20 to 100° C. and the reaction time is usually in a range of 0.1 to 24 hours.

After completion of the reaction, the compound represented by the formula (5) can be isolated by subjecting to post treatment such as extracting a reaction mixture with an organic solvent and drying and concentrating the organic layer. The isolated compound represented by the formula (5) can also be further purified by chromatography, recrystallization, and the like.

Production Process 6

Among the compounds of the present invention, a compound represented by the formula (11) in which $X^1$ is a fluorine atom and $X^2$ is a hydrogen atom can be produced according to the following scheme.

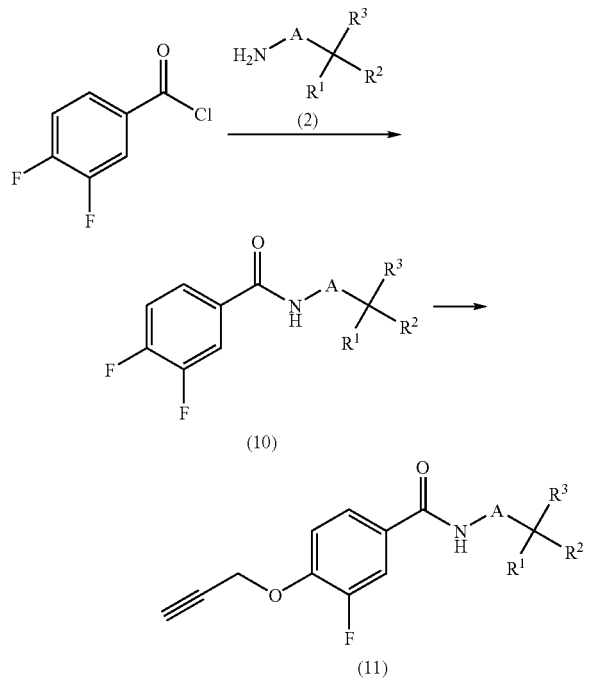

wherein A, $R^1$, $R^2$ and $R^3$ are as defined above.

A compound represented by the formula (10) can be produced by reacting 3,4-difluorobenzoyl chloride with the compound represented by the formula (2) in the presence of a base.

The reaction is usually carried out in the presence of a solvent.

Examples of the solvent used for the reaction include ethers such as THF, ethyleneglycol dimethyl ether, MTBE, etc.; aliphatic hydrocarbons such as hexane, heptane, octane, etc., aromatic hydrocarbons such as toluene, xylene, etc.; halogenated hydrocarbons such as chlorobenzene, etc.; esters such as butyl acetate, ethyl acetate, etc.; ketones such as acetone, methyl ethyl ketone, methyl isobutyl ketone, etc.; nitrites such as acetonitrile, etc.; acid amides such as DMF, etc.; sulfoxides such as dimethylsulfoxide, etc.; and a mixture thereof.

The base used for the reaction includes alkali metal carbonates such as sodium carbonate, potassium carbonate, etc.; tertiary amines such as triethylamine, diisopropylethylamine, etc.; nitrogen-containing aromatic compounds such as pyridine, 4-dimethylaminopyridine, etc.; and the like.

Usually, 3,4-difluorobenzoyl chloride is used at a proportion of 1 to 3 mol and the base is used at a proportion of 1 to 10 mol based on 1 mol of the compound represented by the formula (2).

The reaction temperature is usually in a range of −20 to 100° C. and the reaction time is usually in a range of 0.1 to 24 hours.

After completion of the reaction, the compound represented by the formula (10) can be isolated by subjecting to post treatment such as extracting a reaction mixture with an organic solvent and drying and concentrating the organic layer. The isolated compound represented by the formula (10) can also be further purified by chromatography, recrystallization, and the like.

The compound represented by the formula (11) can be produced by reacting the compound represented by the formula (10) with propargyl alcohol in the presence of a base.

The reaction is usually carried out in the presence of a solvent.

Examples of the solvent used for the reaction include ethers such as THF, ethyleneglycol dimethyl ether, MTBE, etc.; aliphatic hydrocarbons such as hexane, heptane, octane, etc.; ketones such as acetone, methyl ethyl ketone, methyl isobutyl ketone, etc.; aromatic hydrocarbons such as toluene, xylene, etc.; halogenated hydrocarbons such as chlorobenzene, etc.; esters such as butyl acetate, ethyl acetate, etc.; nitrites such as acetonitrile, etc.; acid amides such as DMF, etc.; sulfoxides such as dimethylsulfoxide, etc.; and a mixture thereof.

The base used for the reaction includes alkali metal carbonates such as sodium carbonate, potassium carbonate, etc.; alkali metal bicarbonates such as sodium bicarbonate, etc.; alkali metal hydrides such as sodium hydride, etc.; alkali metal hydroxides such as sodium hydroxide, etc.; and the like.

Usually, propargyl alcohol is used at a proportion of 1 to 3 mol and the base is used at a proportion of 1 to 2 mol based on 1 mol of the compound represented by the formula (10).

The reaction temperature is usually in a range of −20 to 100° C. and the reaction time is usually in a range of 0.1 to 24 hours.

After completion of the reaction, the compound represented by the formula (11) can be isolated by subjecting to post treatment such as extracting a reaction mixture with an organic solvent and drying and concentrating the organic layer. The isolated compound represented by the formula (11) can also be further purified by chromatography, recrystallization, and the like.

An intermediate used for the production of the compound of the present invention can be produced by, for example, the following Intermediate Production Process 1 to Intermediate Production Process 7.

Intermediate Production Process 1

The compound represented by the formula (3) and the compound represented by the formula (4) can be produced according to the following scheme.

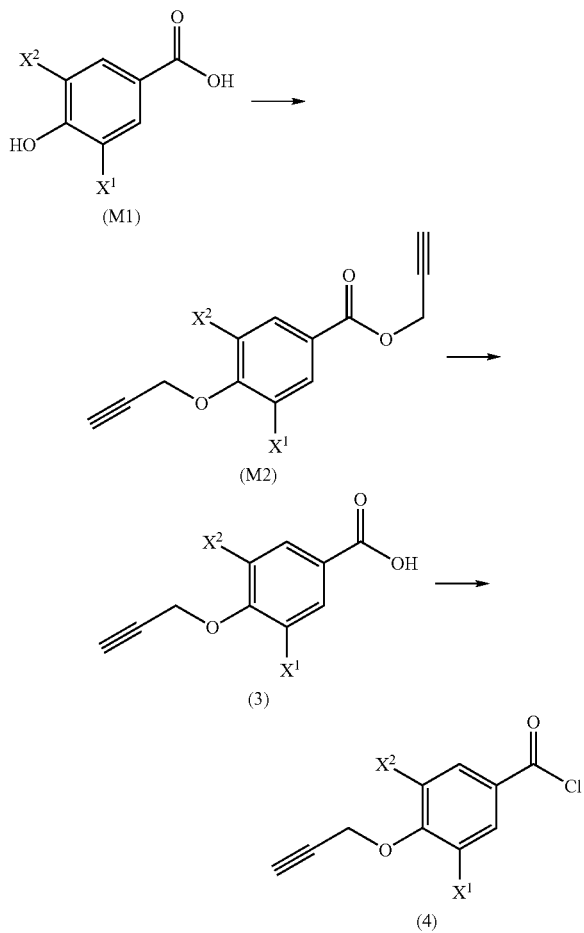

wherein $X^1$ and $X^2$ are as defined above.

A compound represented by the formula (M2) can be produced by reacting the compound represented by the formula (M1) with propargyl bromide in the presence of a base.

The reaction is usually carried out in the presence of a solvent.

Examples of the solvent used for the reaction include acid amides such as DMF, etc.; sulfoxides such as DMSO, etc.

The base used for the reaction includes alkali metal carbonates such as sodium carbonate, potassium carbonate, cesium carbonate, etc.; alkali metal hydroxides such as sodium hydroxide, etc.; and the like.

Usually, propargyl bromide is used at a proportion of 2 to 5 mol and the base is used at a proportion of 2 to 5 mol based on 1 mol of the compound represented by the formula (M1).

The reaction temperature is usually in a range of 0 to 140° C. and the reaction time is usually in a range of 0.5 to 24 hours.

After completion of the reaction, the compound represented by the formula (M2) can be isolated by subjecting to post treatment such as extracting a reaction mixture with an organic solvent and drying and concentrating the organic layer. The isolated compound represented by the formula (M2) can also be further purified by chromatography, recrystallization, and the like.

The compound represented by the formula (3) can be produced by hydrolyzing the compound represented by the formula (M2) in the presence of a base.

The reaction is usually carried out in the presence of a solvent.

The base used for the reaction includes alkali metal hydroxides such as sodium hydroxide, potassium hydroxide, etc.; and the like.

Examples of the solvent used for the reaction include ethers such as tetrahydrofuran, ethyleneglycol dimethyl ether, tert-butyl methyl ether, etc.; alcohols such as methanol, ethanol, etc.; and a mixture thereof.

Water is used at a proportion of 1 mol to an excessive amount and the base is usually used at a proportion of 1 to 10 mol based on 1 mol of the compound represented by the formula (M2).

The reaction temperature is usually in a range of 0 to 120° C. and the reaction time is usually in a range of 0.5 to 24 hours.

After completion of the reaction, the compound represented by the formula (3) can be isolated by subjecting to post treatment such as acidifying a reaction mixture, then extracting it with an organic solvent and drying and concentrating the organic layer. The isolated compound represented by the formula (3) can also be further purified by chromatography, recrystallization, and the like.

The compound represented by the formula (4) can be produced by reacting the compound represented by the formula (3) with thionyl chloride.

The reaction is usually carried out in the presence of a solvent.

Examples of the solvent used for the reaction include aliphatic hydrocarbons such as hexane, heptane, octane, etc.; aromatic hydrocarbons such as toluene, xylene, etc.; nitrites such as acetonitrile, etc.; halogenated hydrocarbons such as chlorobenzene, etc.; acid amides such as DMF, etc.; and a mixture thereof.

Thionyl chloride is usually used at a proportion of 1 to 2 mol based on 1 mol of the compound represented by the formula (3).

The reaction temperature is usually in a range of 20 to 120° C. and the reaction time is usually in a range of 0.1 to 24 hours.

After completion of the reaction, the compound represented by the formula (4) can be isolated by concentrating a reaction mixture as it is.

Intermediate Production Process 2

The compound represented by the formula (9) can be produced according to the following scheme.

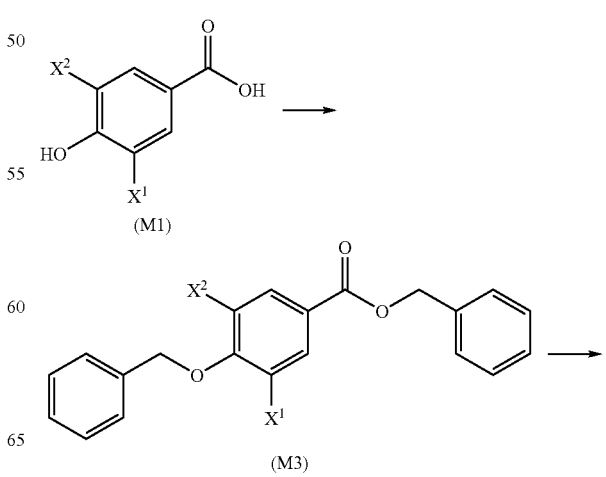

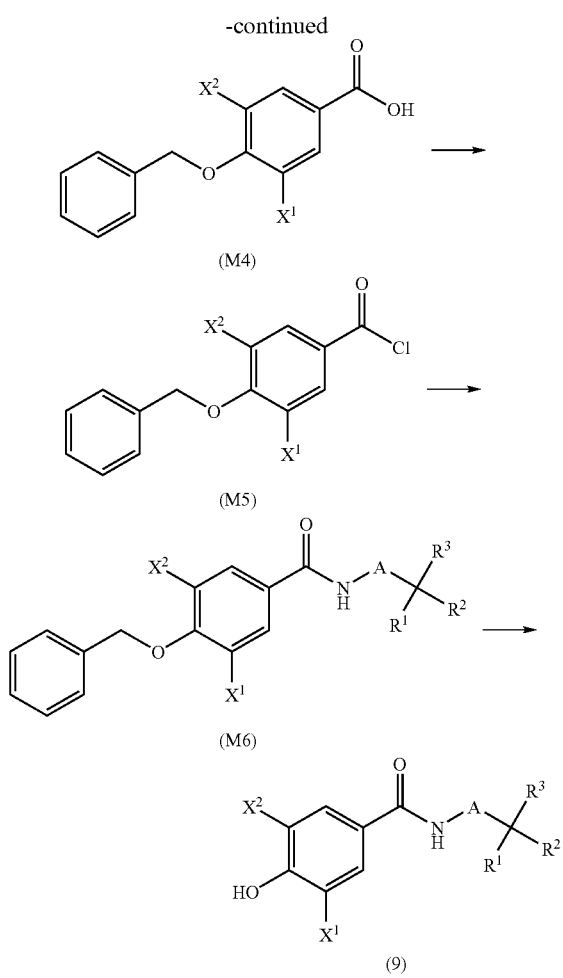

wherein A, $R^1$, $R^2$, $R^3$, $X^1$ and $X^2$ are as defined above.

The compound represented by the formula (M3) can be produced by reacting the compound represented by the formula (M1) with benzyl bromide in the presence of a base.

The reaction is usually carried out in the presence of a solvent.

Examples of the solvent used for the reaction include acid amides such as DMF, etc.; sulfoxides such as DMSO, etc.

Examples of the base used for the reaction include alkali metal carbonates such as sodium carbonate, potassium carbonate, cesium carbonate, etc.; alkali metal hydroxides such as sodium hydroxide, etc.; and the like.

Usually, benzyl bromide is used at a proportion of 2 to 5 mol and the base is used at a proportion of 2 to 5 mol based on 1 mol of the compound represented by the formula (M1).

The reaction temperature is usually in a range of 0 to 140° C. and the reaction time is usually in a range of 0.5 to 24 hours.

After completion of the reaction, the compound represented by the formula (M3) can be isolated by subjecting to post treatment such as extracting a reaction mixture with an organic solvent and drying and concentrating the organic layer. The isolated compound represented by the formula (M3) can also be further purified by chromatography, recrystallization, and the like.

The compound represented by the formula (M4) can be produced by hydrolyzing the compound represented by the formula (M3) in the presence of a base.

The reaction is usually carried out in the presence of a solvent.

Examples of the base used for the reaction include alkali metal hydroxides such as sodium hydroxide, potassium hydroxide, etc.; and the like.

Examples of the solvent used for the reaction include ethers such as tetrahydrofuran, ethyleneglycol dimethyl ether, tert-butyl methyl ether, etc.; alcohols such as methanol, ethanol, etc.; and a mixture thereof.

Water is used at a proportion of 1 mol to an excessive amount and the base is usually used at a proportion of 1 to 10 mol based on 1 mol of the compound represented by the formula (M3).

The reaction temperature is usually in a range of 0 to 120° C. and the reaction time is usually in a range of 0.5 to 24 hours.

After completion of the reaction, the compound represented by the formula (M4) can be isolated by subjecting to post treatment such as acidifying a reaction mixture, then extracting it with an organic solvent and drying and concentrating the organic layer. The isolated compound represented by the formula (M4) can also be further purified by chromatography, recrystallization, and the like.

The compound represented by the formula (M5) can be produced by reacting the compound represented by the formula (M4) with thionyl chloride.

The reaction is usually carried out in the presence of a solvent.

Examples of the solvent used for the reaction include aliphatic hydrocarbons such as hexane, heptane, octane, etc.; aromatic hydrocarbons such as toluene, xylene, etc.; nitrites such as acetonitrile, etc.; halogenated hydrocarbons such as chlorobenzene, etc.; acid amides such as DMF, etc.; and a mixture thereof.

Thionyl chloride is usually used at a proportion of 1 to 2 mol based on 1 mol of the compound represented by the formula (M4).

The reaction temperature is usually in a range of 20 to 120° C. and the reaction time is usually in a range of 0.1 to 24 hours.

After completion of the reaction, the compound represented by the formula (M5) can be isolated by concentrating a reaction mixture as it is.

The compound represented by the formula (M6) can be produced by reacting the compound represented by the formula (M5) with the compound represented by the formula (2) in the presence of a base according to the method described in Production Process 2.

The compound represented by the formula (9) can be produced by reacting the compound represented by the formula (M6) with hydrogen in the presence of palladium-carbon.

The reaction is usually carried out in the presence of a solvent.

Examples of the solvent used for the reaction include aliphatic hydrocarbons such as hexane, heptane, octane, etc.; aromatic hydrocarbons such as toluene, xylene, etc.; alcohols such as methanol, ethanol, etc.; esters such as ethyl acetate. etc.; ethers such as THF, MTBE, etc.; water; and a mixture thereof.

Usually, palladium-carbon is used at a proportion of 0.01 to 0.1 mol and hydrogen is used at a proportion of 1 to 2 mol based on 1 mol of the compound represented by the formula (M6).

The reaction temperature is usually in a range of 0 to 50° C. and the reaction time is usually in a range of 0.1 to 24 hours.

After completion of the reaction, the compound represented by the formula (9) can be isolated by subjecting to post treatment such as filtering a reaction mixture, extracting it with an organic solvent and drying and concentrating the organic layer. The isolated compound represented by the formula (9) can also be further purified by chromatography, recrystallization, and the like.

Intermediate Production Process 3

Among the compounds represented by the formula (9), a compound represented by the formula (9-1) in which A is a single bond can be produced according to the following scheme.

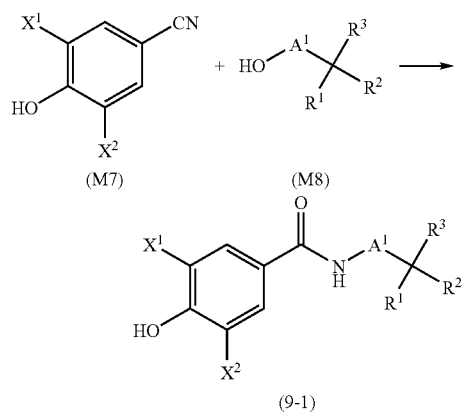

wherein $R^1$, $R^2$, $R^3$, $X^1$ and $X^2$ are as defined above and $A^1$ represents a single bond.

The compound represented by the formula (9-1) can be produced by reacting a compound represented by the formula (M7) with a compound represented by the formula (M8) in the presence of concentrated sulfuric acid.

The reaction is carried out in the presence or absence of a solvent.

Examples of the solvent used for the reaction include aliphatic carboxylic acids such as acetic acid, etc. and a mixture thereof.

Usually, the compound represented by the formula (M8) is usually used at a proportion of 1 to 10 mol and concentrated sulfuric acid is used at a proportion of 1 to 20 mol based on 1 mol of the compound represented by the formula (M7).

The reaction temperature is usually in a range of 0 to 100° C. and the reaction time is usually in a range of 0.5 to 24 hours.

After completion of the reaction, the compound represented by the formula (9-1) can be isolated by subjecting to post treatment such as extracting a reaction mixture with an organic solvent and drying and concentrating the organic layer. The isolated compound represented by the formula (9-1) can also be further purified by chromatography, recrystallization, and the like.

Among the compounds represented by the formula (3), the compound in which $X^1$ and $X^2$ are a fluorine atom, i.e., 3,5-difluoro-4-(2-propynyloxy)benzoic acid, can be produced by the process described in Intermediate Production Process 4 or Intermediate Production Process 5 from 3,4,5-trifluorobenzaldehyde.

Intermediate Production Process 4

3,5-Difluoro-4-(2-propynyloxy)benzoic acid can be produced according to the following scheme.

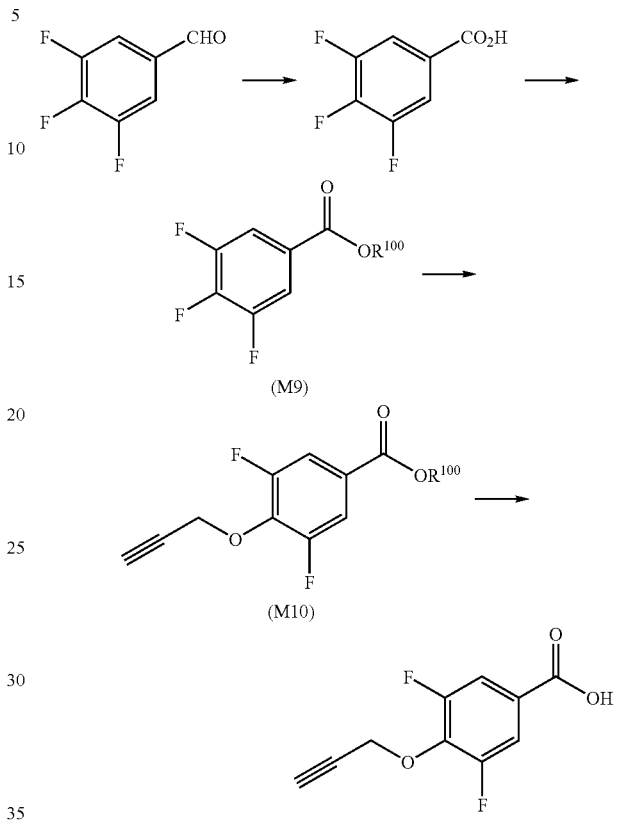

wherein $R^{100}$ represents a C1-C4 alkyl group, a 2-propynyl group or a benzyl group.

3,4,5-Trifluorobenzoic acid can be produced by reacting 3,4,5-trifluorobenzaldehyde with an oxidizing agent.

The reaction is usually carried out in the presence of a solvent.

Examples of the solvent used for the reaction include ketones such as acetone, methyl ethyl ketone, methyl isobutyl ketone, etc.; nitriles such as acetonitrile, etc.; acid amides such as DMF, etc.; halogenated hydrocarbons such as chloroform, etc.; water; and a mixture thereof.

Examples of the oxidizing agent used for the reaction include potassium permanganate, 3-chloroperbenzoic acid and potassium peroxymonosulfate.

The oxidizing agent is usually used at a proportion of 1 to 5 mol based on 1 mol of 3,4,5-trifluorobenzaldehyde.

The reaction temperature is usually in a range of 0 to 100° C. and the reaction time is usually in a range of 0.5 to 24 hours.

After completion of the reaction, 3,4,5-trifluorobenzoic acid can be isolated by subjecting to post treatment such as extracting a reaction mixture with an organic solvent and drying and concentrating the organic layer. The isolated 3,4,5-trifluorobenzoic acid can also be further purified by chromatography, recrystallization, and the like.

The compound represented by the formula (M9) can be produced by reacting 3,4,5-trifluorobenzoic acid with $R^{100}$-$L^1$ (wherein $L^1$ represents a chlorine atom, a bromine atom, an iodine atom or a methanesulfonyloxy group) in the presence of a base.

The reaction is usually carried out in the presence of a solvent.

Examples of the solvent used for the reaction include nitrites such as acetonitrile, etc.; acid amides such as DMF, etc.; sulfoxides such as DMSO, etc.; and a mixture thereof.

Examples of the base used for the reaction include alkali metal carbonates such as sodium carbonate, potassium carbonate, cesium carbonate, etc.; alkali metal hydroxides such as sodium hydroxide, etc.; and the like.

Usually, the compound represented by $R^{100}$-$L^1$ is used at a proportion of 1 to 5 mol and the base is used at a proportion of 1 to 5 mol based on 1 mol of 3,4,5-trifluorobenzoic acid.

The reaction temperature is usually in a range of 0 to 140° C. and the reaction time is usually in a range of 0.5 to 24 hours.

After completion of the reaction, the compound represented by the formula (M9) can be isolated by subjecting to post treatment such as extracting a reaction mixture with an organic solvent and drying and concentrating the organic layer. The isolated compound represented by the formula (M9) can also be further purified by chromatography, recrystallization, and the like.

The compound represented by the formula (M10) can be produced by reacting the compound represented by the formula (M9) with propargyl alcohol in the presence of a base.

The reaction is usually carried out in the presence of a solvent.

Examples of the solvent used for the reaction include nitrites such as acetonitrile, etc.; acid amides such as DMF, etc.; sulfoxides such as DMSO, etc.

The base used for the reaction includes alkali metal carbonates such as sodium carbonate, potassium carbonate, cesium carbonate, etc.; alkali metal hydroxides such as sodium hydroxide, etc.; alkali metal hydrides such as sodium hydride, etc.; and the like.

Usually, propargyl alcohol is used at a proportion of 1 to 5 mol and the base is used at a proportion of 1 to 5 mol based on 1 mol of the compound represented by the formula (M9).

The reaction temperature is usually in a range of 0 to 140° C. and the reaction time is usually in a range of 0.5 to 24 hours.

After completion of the reaction, the compound represented by the formula (M10) can be isolated by subjecting to post treatment such as extracting a reaction mixture with an organic solvent and drying and concentrating the organic layer. The isolated compound represented by the formula (M10) can also be further purified by chromatography, recrystallization, and the like.

3,5-Difluoro-4-(2-propynyloxy)benzoic acid can be produced by hydrolyzing the compound represented by the formula (M10) in the presence of a base.

The reaction is usually carried out in the presence of a solvent.

Examples of the base used for the reaction include alkali metal hydroxides such as sodium hydroxide, potassium hydroxide, etc.; and the like.

Examples of the solvent used for the reaction include ethers such as tetrahydrofuran, ethyleneglycol dimethyl ether, tert-butyl methyl ether, etc.; alcohols such as methanol, ethanol, etc.; and a mixture thereof.

Usually, water is used at a proportion of 1 mol to an excessive amount and the base is used at a proportion of 1 to 10 mol based on 1 mol of the compound represented by the formula (M10).

The reaction temperature is usually in a range of 0 to 120° C. and the reaction time is usually in a range of 0.5 to 24 hours.

After completion of the reaction, 3,5-difluoro-4-(2-propynyloxy)benzoic acid can be isolated by subjecting to post treatment such as acidifying a reaction mixture, then extracting it with an organic solvent and drying and concentrating the organic layer. The isolated 3,5-difluoro-4-(2-propynyloxy)benzoic acid can also be further purified by chromatography, recrystallization, and the like.

Intermediate Production Process 5

3,5-Difluoro-4-(2-propynyloxy)benzoic acid can be produced according to the following scheme.

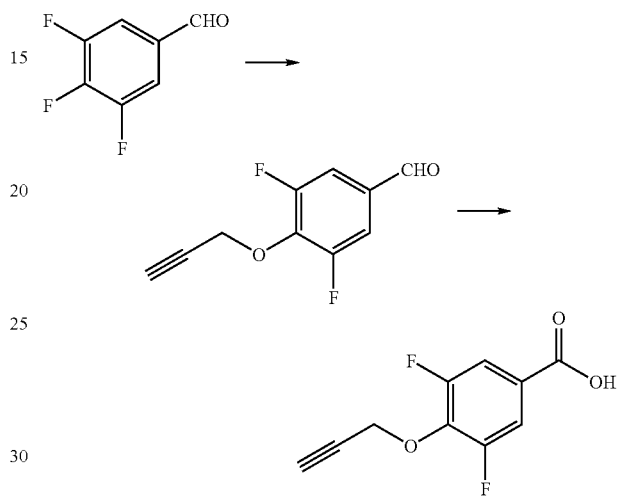

3,5-Difluoro-4-(2-propynyloxy)benzaldehyde can be produced by reacting 3,4,5-trifluorobenzaldehyde with propargyl alcohol in the presence of a base.

The reaction is usually carried out in the presence of a solvent.

Examples of the solvent used for the reaction include hydrocarbons such as toluene, etc.; nitrites such as acetonitrile, etc.; acid amides such as DMF, etc.; sulfoxides such as DMSO, etc.; ketones such as acetone, methyl ethyl ketone, methyl isobutyl ketone, etc.; water; and a mixture thereof.

The base used for the reaction includes alkali metal carbonates such as sodium carbonate, potassium carbonate, cesium carbonate, etc.; alkali metal hydroxides such as sodium hydroxide, etc.; alkali metal hydrides such as sodium hydride, etc.; and the like.

Usually, propargyl alcohol is used at a proportion of 1 to 5 mol and the base is used at a proportion of 1 to 5 mol based on 1 mol of 3,4,5-trifluorobenzaldehyde.

The reaction temperature is usually in a range of 0 to 100° C. and the reaction time is usually in a range of 0.5 to 24 hours.

After completion of the reaction, 3,5-difluoro-4-(2-propynyloxy)benzaldehyde can be isolated by subjecting to post treatment such as extracting a reaction mixture with an organic solvent and drying and concentrating the organic layer. The isolated 3,5-difluoro-4-(2-propynyloxy)benzaldehyde can also be further purified by chromatography, recrystallization, and the like.

3,5-Difluoro-4-(2-propynyloxy)benzoic acid can be produced by reacting 3,5-difluoro-4-(2-propynyloxy)benzaldehyde with an oxidizing agent.

The reaction is usually carried out in the presence of a solvent.

Examples of the solvent used for the reaction include ketones such as acetone, methyl ethyl ketone, methyl isobutyl ketone, etc.; nitriles such as acetonitrile, etc.; acid amides such as DMF, etc.; halogenated hydrocarbons such as chloroform, etc.; water; and a mixture thereof.

Examples of the oxidizing agent used for the reaction include potassium permanganate, 3-chloroperbenzoic acid and potassium peroxymonosulfate.

Usually, the oxidizing agent is used at a proportion of 1 to 5 mol based on 1 mol of 3,5-difluoro-4-(2-propynyloxy)benzaldehyde.

The reaction temperature is usually in a range of 0 to 100° C. and the reaction time is usually in a range of 0.5 to 24 hours.

After completion of the reaction, 3,5-difluoro-4-(2-propynyloxy)benzoic acid can be isolated by subjecting to post treatment such as extracting a reaction mixture with an organic solvent and drying and concentrating the organic layer. The isolated 3,5-difluoro-4-(2-propynyloxy)benzoic acid can also be further purified by chromatography, recrystallization, and the like.

Intermediate Production Process 6

Among the compounds represented by the formula (2), the compound in which A is a methylene group can be produced by reacting a compound represented by the formula (M21) or a compound represented by the formula (M22) with a reducing agent (for example, lithium aluminum hydride).

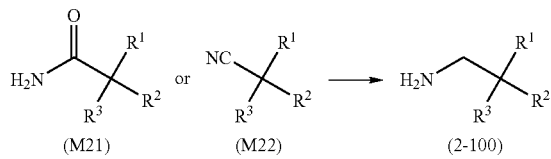

wherein $R^1$, $R^2$ and $R^3$ are as defined above.

The reaction is usually carried out in the presence of a solvent.

Examples of the solvent used for the reaction include ethers such as THF, ethyleneglycol dimethyl ether and MTBE and the like.

The reducing agent is usually used at a proportion of 0.5 to 3 mol based on 1 mol of the compound represented by the formula (M21) or the compound represented by the formula (M22).

The reaction temperature is usually in a range of −20 to 100° C. and the reaction time is usually in a range of 0.1 to 24 hours.

After completion of the reaction, the compound represented by the formula (2-100) can be isolated by subjecting to post treatment such as extracting a reaction mixture with an organic solvent and drying and concentrating the organic layer. The isolated compound represented by the formula (2-100) can also be further purified by chromatography, recrystallization, and the like.

Intermediate Production Process 7

Among the compounds represented by the formula (2), the compound in which A is a single bond and $R^3$ is a hydrogen can be produced by reacting a compound represented by the formula (M23) with ammonium formate in the presence of a transition metal catalyst (for example, palladium-carbon).

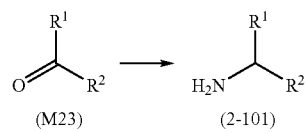

wherein $R^1$ and $R^2$ are as defined above.

The reaction is usually carried out in the presence of a solvent.

Examples of the solvent used for the reaction include ethers such as THF, ethyleneglycol dimethyl ether, MTBE, etc.; alcohols such as methanol, ethanol, etc; water and the like.

Usually, ammonium formate is used at a proportion of 1 to 10 mol and the transition metal catalyst is used at a proportion of 0.001 to 0.1 mol based on 1 mol of the compound represented by the formula (M23).

The reaction temperature is usually in a range of 0 to 100° C. and the reaction time is usually in a range of 0.1 to 24 hours.

After completion of the reaction, the compound represented by the formula (2-101) can be isolated by subjecting to post treatment such as extracting a reaction mixture with an organic solvent and drying and concentrating the organic layer. The isolated compound represented by the formula (2-101) can also be further purified by chromatography, recrystallization, and the like.

The compound represented by the formula (2) can also be produced according to a method described in "Experimental Chemistry Course" 4th Edition 20, pp 279-318 (published by MARUZEN).

Then, specific examples of the compounds of the present invention are shown below. Further, a methyl group is occasionally described as Me and an ethyl group is occasionally described as Et below.

The compound represented by the formula (E1):

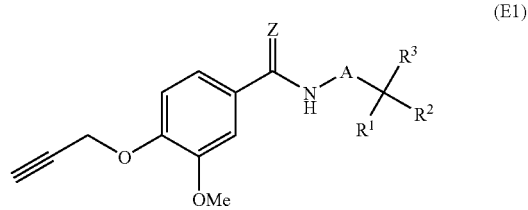

In the above-mentioned formula (E1), the respective substituents of A, $R^1$, $R^2$, $R^3$ and Z are the combinations described in Table 1 to Table 6.

TABLE 1

| A | Z | $R^1$ | $R^2$ | $R^3$ |
|---|---|---|---|---|
| — | O | Me | Me | Me |
| — | O | Me | Et | Me |
| — | O | Me | $CH_2CH_2CH_3$ | Me |
| — | O | Me | $CH(CH_3)_2$ | Me |
| — | O | Me | $CH_2CH_2CH_2CH_3$ | Me |
| — | O | Me | Me | C≡CH |
| — | O | Me | Me | CH=$CH_2$ |
| — | O | Me | Me | $CO_2H$ |
| — | O | Me | Me | $CO_2Et$ |
| — | O | Me | Me | H |
| — | O | Me | Et | H |

TABLE 1-continued

| A | Z | R¹ | R² | R³ |
|---|---|----|----|----|
| — | O | Me | $CH_2CH_2CH_3$ | H |
| — | O | Me | $CH(CH_3)_2$ | H |
| — | O | Me | $CH_2CH_2CH_2CH_3$ | H |
| — | O | Me | $CH(CH_3)CH_2CH_3$ | H |
| — | O | Me | $CH_2CH(CH_3)_2$ | H |
| — | O | Me | $C(CH_3)_3$ | H |
| — | O | Et | Et | H |
| — | O | Et | $CH_2CH_2CH_3$ | H |
| — | O | Et | $CH(CH_3)_2$ | H |
| — | O | Et | $CH_2CH_2CH_2CH_3$ | H |
| — | O | Et | $CH(CH_3)CH_2CH_3$ | H |
| — | O | Et | $CH_2CH(CH_3)_2$ | H |
| — | O | Et | $C(CH_3)_3$ | H |

TABLE 2

| A | Z | R¹ | R² | R³ |
|---|---|----|----|----|
| — | O | $CH_2CH_2CH_3$ | $CH_2CH_2CH_3$ | H |
| — | O | $CH_2CH_2CH_3$ | $CH(CH_3)_2$ | H |
| — | O | $CH(CH_3)_2$ | $CH(CH_3)_2$ | H |
| — | O | $CH(CH_3)_2$ | $CH_2CH_2CH_2CH_3$ | H |
| — | O | $CH(CH_3)_2$ | $CH(CH_3)CH_2CH_3$ | H |
| — | O | $CH(CH_3)_2$ | $CH_2CH(CH_3)_2$ | H |
| — | O | Me | Me | CN |
| — | O | Me | Et | CN |
| — | O | Me | $CH_2CH_2CH_3$ | CN |
| — | O | Me | $CH(CH_3)_2$ | CN |
| — | O | Me | $CH_2CH_2CH_2CH_3$ | CN |
| — | O | Me | $CH(CH_3)CH_2CH_3$ | CN |
| — | O | Me | $CH_2CH(CH_3)_2$ | CN |
| — | O | Me | $C(CH_3)_3$ | CN |
| — | O | Me | Me | $CO_2Me$ |
| — | O | Me | Et | $CO_2Me$ |
| — | O | Me | $CH_2CH_2CH_3$ | $CO_2Me$ |
| — | O | Me | $CH(CH_3)_2$ | $CO_2Me$ |
| — | O | Me | $CH_2CH_2CH_2CH_3$ | $CO_2Me$ |
| — | O | Me | $CH(CH_3)CH_2CH_3$ | $CO_2Me$ |
| — | O | Me | $CH_2CH(CH_3)_2$ | $CO_2Me$ |
| — | O | Me | $C(CH_3)_3$ | $CO_2Me$ |
| — | O | Et | Et | CN |
| — | O | Et | Et | $CO_2Me$ |

TABLE 3

| A | Z | R¹ | R² | R³ |
|---|---|----|----|----|
| $CH_2$ | O | Me | Me | Me |
| $CH_2$ | O | Me | Et | Me |
| $CH_2$ | O | Me | $CH_2CH_2CH_3$ | Me |
| $CH_2$ | O | Me | $CH(CH_3)_2$ | Me |
| $CH_2$ | O | Me | $CH_2CH_2CH_2CH_3$ | Me |
| $CH_2$ | O | Me | Me | C≡CH |
| $CH_2$ | O | Me | Me | CH=$CH_2$ |
| $CH_2$ | O | Me | Me | $CO_2H$ |
| $CH_2$ | O | Me | Me | $CO_2Et$ |
| $CH_2$ | O | Me | Me | H |
| $CH_2$ | O | Me | Et | H |
| $CH_2$ | O | Me | $CH_2CH_2CH_3$ | H |
| $CH_2$ | O | Me | $CH(CH_3)_2$ | H |
| $CH_2$ | O | Me | $CH_2CH_2CH_2CH_3$ | H |
| $CH_2$ | O | Me | $CH(CH_3)CH_2CH_3$ | H |
| $CH_2$ | O | Me | $CH_2CH(CH_3)_2$ | H |
| $CH_2$ | O | Me | $C(CH_3)_3$ | H |
| $CH_2$ | O | Et | Et | H |
| $CH_2$ | O | Et | $CH_2CH_2CH_3$ | H |
| $CH_2$ | O | Et | $CH(CH_3)_2$ | H |
| $CH_2$ | O | Et | $CH_2CH_2CH_2CH_3$ | H |
| $CH_2$ | O | Et | $CH(CH_3)CH_2CH_3$ | H |
| $CH_2$ | O | Et | $CH_2CH(CH_3)_2$ | H |
| $CH_2$ | O | Et | $C(CH_3)_3$ | H |

TABLE 4

| A | Z | R¹ | R² | R³ |
|---|---|----|----|----|
| $CH_2$ | O | $CH_2CH_2CH_3$ | $CH_2CH_2CH_3$ | H |
| $CH_2$ | O | $CH_2CH_2CH_3$ | $CH(CH_3)_2$ | H |
| $CH_2$ | O | $CH(CH_3)_2$ | $CH(CH_3)_2$ | H |
| $CH_2$ | O | $CH(CH_3)_2$ | $CH_2CH_2CH_2CH_3$ | H |
| $CH_2$ | O | $CH(CH_3)_2$ | $CH(CH_3)CH_2CH_3$ | H |
| $CH_2$ | O | $CH(CH_3)_2$ | $CH_2CH(CH_3)_2$ | H |
| $CH_2$ | O | Me | Me | CN |
| $CH_2$ | O | Me | Et | CN |
| $CH_2$ | O | Me | $CH_2CH_2CH_3$ | CN |
| $CH_2$ | O | Me | $CH(CH_3)_2$ | CN |
| $CH_2$ | O | Me | $CH_2CH_2CH_2CH_3$ | CN |
| $CH_2$ | O | Me | $CH(CH_3)CH_2CH_3$ | CN |
| $CH_2$ | O | Me | $CH_2CH(CH_3)_2$ | CN |
| $CH_2$ | O | Me | $C(CH_3)_3$ | CN |
| $CH_2$ | O | Me | Me | $CO_2Me$ |
| $CH_2$ | O | Me | Et | $CO_2Me$ |
| $CH_2$ | O | Me | $CH_2CH_2CH_3$ | $CO_2Me$ |
| $CH_2$ | O | Me | $CH(CH_3)_2$ | $CO_2Me$ |
| $CH_2$ | O | Me | $CH_2CH_2CH_2CH_3$ | $CO_2Me$ |
| $CH_2$ | O | Me | $CH(CH_3)CH_2CH_3$ | $CO_2Me$ |
| $CH_2$ | O | Me | $CH_2CH(CH_3)_2$ | $CO_2Me$ |
| $CH_2$ | O | Me | $C(CH_3)_3$ | $CO_2Me$ |
| $CH_2$ | O | Et | Et | CN |
| $CH_2$ | O | Et | Et | $CO_2Me$ |

TABLE 5

| A | Z | R¹ | R² | R³ |
|---|---|----|----|----|
| — | S | Me | Me | Me |
| — | S | Me | Et | Me |
| — | S | Me | $CH_2CH_2CH_3$ | Me |
| — | S | Me | $CH(CH_3)_2$ | Me |
| — | S | Me | Me | H |
| — | S | Me | Et | H |
| — | S | Me | $CH_2CH_2CH_3$ | H |
| — | S | Me | $CH(CH_3)_2$ | H |
| — | S | Me | $CH(CH_3)CH_2CH_3$ | H |
| — | S | Me | $CH_2CH(CH_3)_2$ | H |
| — | S | Me | $C(CH_3)_3$ | H |
| — | S | Et | Et | H |
| — | S | Et | $CH_2CH_2CH_3$ | H |
| — | S | Et | $CH(CH_3)_2$ | H |
| — | S | Et | $CH(CH_3)CH_2CH_3$ | H |
| — | S | Et | $CH_2CH(CH_3)_2$ | H |
| — | S | Et | $C(CH_3)_3$ | H |
| — | S | $CH_2CH_2CH_3$ | $CH_2CH_2CH_3$ | H |
| — | S | $CH_2CH_2CH_3$ | $CH(CH_3)_2$ | H |
| — | S | $CH(CH_3)_2$ | $CH(CH_3)_2$ | H |
| — | S | $CH(CH_3)_2$ | $CH(CH_3)CH_2CH_3$ | H |
| — | S | $CH(CH_3)_2$ | $CH_2CH(CH_3)_2$ | H |
| $CH_2$ | S | Me | Me | Me |
| $CH_2$ | S | Me | Et | Me |

TABLE 6

| A | Z | R¹ | R² | R³ |
|---|---|----|----|----|
| $CH_2$ | S | Me | $CH_2CH_2CH_3$ | Me |
| $CH_2$ | S | Me | $CH(CH_3)_2$ | Me |
| $CH_2$ | S | Me | Me | H |
| $CH_2$ | S | Me | Et | H |
| $CH_2$ | S | Me | $CH_2CH_2CH_3$ | H |
| $CH_2$ | S | Me | $CH(CH_3)_2$ | H |
| $CH_2$ | S | Me | $CH(CH_3)CH_2CH_3$ | H |
| $CH_2$ | S | Me | $CH_2CH(CH_3)_2$ | H |
| $CH_2$ | S | Me | $C(CH_3)_3$ | H |
| $CH_2$ | S | Et | Et | H |
| $CH_2$ | S | Et | $CH_2CH_2CH_3$ | H |
| $CH_2$ | S | Et | $CH(CH_3)_2$ | H |
| $CH_2$ | S | Et | $CH(CH_3)CH_2CH_3$ | H |
| $CH_2$ | S | Et | $CH_2CH(CH_3)_2$ | H |

TABLE 6-continued

| A | Z | R¹ | R² | R³ |
|---|---|---|---|---|
| $CH_2$ | S | Et | $C(CH_3)_3$ | H |
| $CH_2$ | S | $CH_2CH_2CH_3$ | $CH_2CH_2CH_3$ | H |
| $CH_2$ | S | $CH_2CH_2CH_3$ | $CH(CH_3)_2$ | H |
| $CH_2$ | S | $CH(CH_3)_2$ | $CH(CH_3)_2$ | H |
| $CH_2$ | S | $CH(CH_3)_2$ | $CH_2CH_2CH_2CH_3$ | H |
| $CH_2$ | S | $CH(CH_3)_2$ | $CH(CH_3)CH_2CH_3$ | H |
| $CH_2$ | S | $CH(CH_3)_2$ | $CH_2CH(CH_3)_2$ | H |

(In the above-mentioned Tables 1 to 6, — represents a single bond.)

The compound represented by the formula (E2):

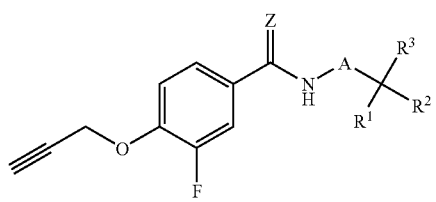

(E2)

In the above-mentioned formula (E2), the respective substituents of A, R¹, R², R³ and Z are the combinations described in Table 1 to Table 6.

The compound represented by the formula (E3):

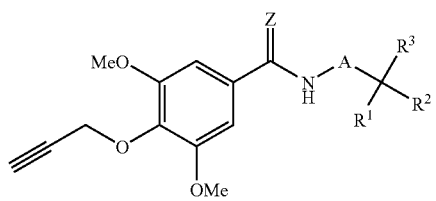

(E3)

In the above-mentioned formula (E3), the respective substituents of A, R¹, R², R³ and Z are the combinations described in Table 1 to Table 6.

The compound represented by the formula (E4):

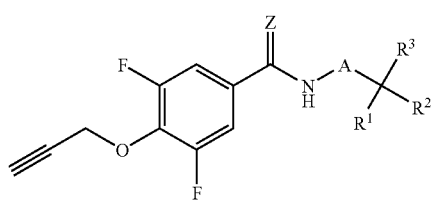

(E4)

In the above-mentioned formula (E4), the respective substituents of A, R¹, R², R³ and Z are the combinations described in Table 1 to Table 6.

The compound represented by the formula (E5):

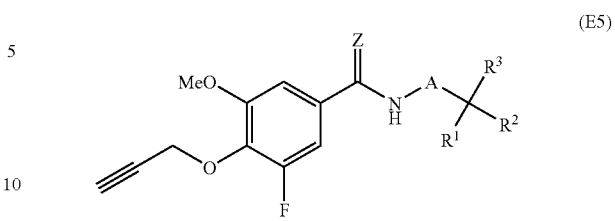

(E5)

In the above-mentioned formula (E5), the respective substituents of A, R¹, R², R³ and Z are the combinations described in Table 1 to Table 6.

Examples of plant diseases for which the compound of the present invention has controlling activity include plant diseases by *Phycomycetes* (*Oomycetes*), plant diseases by fungi and plant diseases by bacteria and specifically include the followings:

*Pyricularia oryzae*, *Cochliobolus miyabeanus* and *Rhizoctonia solani* of rice plant;

*Erysiphe graminis*, *Gibberella zeae*, *Puccinia striiformis*, *P. graminis*, *P. recondita*, *P. hordei*, *Typhula* sp., *Micronectriella nivalis*, *Ustilago tritici*, *U. nuda*, *Tilletia caries*, *Pseudocercosporella herpotrichoides*, *Rhynchosporium secalis*, *Septoria tritici* and *Leptosphaeria nodorum* of wheat, barley, rye and oats;

*Diaporthe citri*, *Elsinoe fawcetti*, *Penicillium digitatum* and *P. italicum* of citrus;

*Sclerotinia mali*, *Valsa mali*, *Podosphaera leucotricha*, *Alternaria mali* and *Venturia inaequalis* of apple;

*Venturia nashicola*, *V. pirina*, *Alternaria kikuchiana* and *Gymnosporangium haraeanum* of pear;

*Sclerotinia cinerea*, *Cladosporium carpophilum* and *Phomopsis* sp. of peach;

*Elsinoe ampelina*, *Glomerella cingulata*, *Uncinula necator*, *Phakopsora ampelopsidis*, *Guignardia bidwellii* and *Plasmopara viticola* of grape;

*Gloeosporium kaki*, *Cercospora kaki* and *Mycosphaerella nawae* of Japanese persimmon;

*Colletotrichum lagenarium*, *Sphaerotheca fuliginea*, *Mycosphaerella melonis*, *Fusarium oxysporum*, *Pseudoperonospora cubensis*, *Phytophthora* sp. and *Pythium* sp. of gourd;

*Alternaria solani*, *Cladosporium fulvum* and *Phytophthora infestans* of tomato;

*Phomopsis vexans* and *Erysiphe cichoracearum* of eggplant;

*Alternaria japonica* and *Cercosporella brassicae* of Cruciferae;

*Puccinia allii* of leek;

*Cercospora kikuchii*, *Elsinoe glycines* and *Diaporthe phaseolorum* var. *sojae* of soybean;

*Colletotrichum lindemthianum* of butter bean;

*Cercospora personata* and *Cercospora arachidicola* of peanut;

*Erysiphe pisi* of pea;

*Alternaria solani* and *Phytophthora infestans* of potato;

*Sphaerotheca humuli* of strawberry;

*Exobasidium reticulatum* and *Elsinoe leucospila* of tea;

*Alternaria longipes, Erysiphe cichoracearum, Colletotrichum tabacum, Peronospora tabacina* and *Phytophthora nicotianae* of tobacco;

*Cercospora beticola* of sugar beet;

*Diplocarpon rosae* and *Sphaerotheca pannosa* of rose;

*Septoria chrysanthemi-indici* and *Puccinia horiana* of crythansumum; and

*Botrytis cinerea* and *Sclerotinia sclerotiorum* of various crops.

The composition for controlling plant diseases of the present invention comprises the compound of the present invention as an effective ingredient and an inactive carrier. Usually, the composition for controlling plant diseases of the present invention is a preparation in the form of emulsion, wettable powder, water dispersible granule, flowable agent, dust, granules, etc., which is prepared by mixing the compound of the present invention, an inactive carrier (solid carrier, liquid carrier and the like), and, if necessary, a surfactant and other adjuvants for preparation. These preparations contain usually 0.1 to 90% by weight of the compound of the present invention.

Examples of the solid carrier used for the preparation include fine powder or granules composed of minerals such as kaoline clay, attabalgite clay, bentonite, montmorillonite, acidic white clay, pyrofillite, talc, diatom earth, lime stones, etc.; natural organic materials such as corn cob powder, walnut shell powder, etc.; synthetic organic materials such as urea, etc.; salts such as calcium carbonate, ammonium sulfate, etc.; synthetic inorganic materials such as synthetic hydrated silicon oxide, etc. Examples of the liquid carrier include aromatic hydrocarbons such as xylene, alkylbenzene, methylnaphthalene, etc.; alcohols such as 2-propanol, ethylene glycol, propylene glycol, ethylene glycol monomethyl ether, etc.; ketones such as acetone, cyclohexane, isophorone, etc.; vegetable oils such as soy bean oil, cotton seed oil, etc.; aliphatic hydrocarbons; esters; dimethylsulfoxide; acetonitrile; and water.

Examples of the surfactant include anionic surfactants such as a salt of alkyl sulfate, a salt of alkylaryl sulfonate, a salt of dialkylsulfo succinate, a salt of polyoxyethylenealkylaryl ether phosphoric acid ester, a salt of lignin sulfonate, a naphthalene sulfonate and formaldehyde polycondensation, etc.; and nonionic surfactants such as polyoxyethylenealkyl aryl ether, polyoxyethylenealkyl polyoxypropylene block copolymer, a fatty acid ester of sorbitan, etc.

Examples of other adjuvants for preparation include water-soluble polymers such as polyvinyl alcohol, polyvinyl pyrrolidone, etc.; polysaccharides such as gum arabic, arginic acid and its salt, CMC (carboxymethylcellulose), xanthan gum, etc.; inorganic substances such as aluminum magnesium silicate, alumina sol, etc.; an antiseptic agent; a colorant; and stabilizers such as PAP (acidic isopropyl phosphate), BHT, etc.

The composition for controlling plant diseases of the present invention is used, for example, for protecting a plant from plant diseases by treating the plant itself, and by treating soil from which used for protecting a plant grown in soil where the plant is growing.

When the composition for controlling plant diseases of the present invention is used for treating the stem or leaves of a plant, or when it is used for treating soil, the amount to be used can be changed depending on the kind of an objective crop, the kind and severity of an objective disease to be treated, the form of a preparation, the treatment timing, weather conditions, and the like, but the amount is usually 1 to 5000 g, preferably 5 to 1000 g per 10,000 $m^2$ in terms of the compound of the present invention.

In case of using emulsion, wettable powder, flowable agent or the like for treatment, it is diluted with water and sprayed. In this case, the concentration of the compound of the present invention is usually in a range of 0.0001 to 3% by weight and preferably 0.0005 to 1% by weight. Dusts and granules are usually treated as they are without being diluted.

Further, the composition for controlling plant diseases of the present invention can also be used in a seed disinfection method, and the like. Examples of the seed disinfection method include immersion of seeds of a plant in the composition for controlling plant diseases of the present invention at concentration of 1 to 1,000 ppm in terms of the compound of the present invention; spraying or coating of the composition for controlling plant diseases of the present invention on seeds of a plant at concentration of 1 to 1,000 ppm in terms of the compound of the present invention; and coating on seeds of a plant with the composition for controlling plant diseases of the present invention in the form of dust.

Usually, the method of controlling plant diseases of the present invention is carried out by treating a plant which is suspected of contraction of a plant disease or soil where such a plant is growing, and/or a plant which is confirmed to contract a plant disease or soil where such a plant is growing with an effective amount of the composition for controlling plant diseases of the present invention.

The composition for controlling plant diseases of the present invention is usually used as a plant disease-controlling preparation for agricultural gardening, that is, a plant disease-controlling plant disease preparation for controlling plant diseases of a field, a paddy field, a fruit orchard, a tea field, a meadow, a turf glass field, and the like.

The composition for controlling plant diseases of the present invention can also be used together with other plant disease-controlling preparations, insecticidal preparations, acaricidal preparations, nematicidal preparations, herbicides, plant growth regulating preparations and/or fertilizers.

Examples of the effective ingredient of such plant disease-controlling preparation include chlorothalonil, fluazinam, dichlofluanide, phosethyl-A1, cyclic imido derivatives (captan, captafol, folpet, and the like), dithiocarbamate derivatives (maneb, mancozeb, thiram, ziram, zineb, propineb, and the like), inorganic or organic copper derivatives (basic copper sulfate, basic copper chloride, copper hydroxide, oxine-copper, and the like), acyl alanine derivatives (metalaxyl, furalaxyl, ofurace, cyprofuram, benalaxyl, oxadixyl, and the like), strobilurin like compounds (kresoxim-methyl, azoxystrobin, trifloxystrobin, picoxystrobin, pyraclostrobin, dimoxystrobin, and the like), anilinopyridine derivatives (cyprodinil, pyrimethanil, mepanipyrim, and the like), phenylpyrrole derivative (fenpiclonil, fludioxonil, and the like), imido derivatives (procymidone, iprodione, vinclozolin, and the like), benzimidazole derivatives (carbendazime, benomyl, thiabendazole, thiophanate-methyl, and the like), amine derivatives (fenpropimorph, tridemorph, fenpropidine, spiroxamine, and the like), azole derivatives (propiconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanole, imazalil, flutriafol, prothioconazole, and the like), propamocarbe, cymoxanil, dimethomorph, famoxadone, fenamidone, pyribencarb, iprovalicarb, benthiavalicarb, mandipropamide, cyazofamid, amisulbrom, zoxamide, ethaboxam, boscalid, fenhexamid, quinoxyfen, proquinazid, metrafenone, cyflufenamid, diethofencarb, fluopicolide and acibenzolar-S-methyl.

Hereinafter, the present invention will be illustrated in more detail by Production Examples, Preparation Examples, Test Examples and the like, but the present invention is not limited thereto.

First, the production of the compounds of the present invention will be illustrated by Production Examples.

PRODUCTION EXAMPLE 1

A mixture of 0.14 g of 2,2-dimethylpropylamine, 0.16 g of triethylamine and 1 ml of ethyl acetate was added dropwise under ice cooling to a mixture of 3 ml of ethyl acetate and 0.30 g of 4-(2-propynyloxy)-3-methoxybenzoyl chloride. The mixture obtained was stirred at room temperature for 4 hours. Ethyl acetate was added to the reaction mixture, it was filtered through Celite and the filtrate was concentrated under reduced pressure. The residue obtained was subjected to silica gel column chromatography to obtain 0.36 g of N-(2,2-diemthylpropyl)-4-(2-propynyloxy)-3-methoxybenzamide (hereinafter, described as the compound 1 of the present invention) represented by the formula:

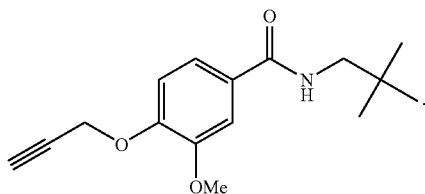

The compound 1 of the present invention:
$^1$H-NMR (CDCl$_3$) δ: 0.98 (9H, s), 2.53 (1H, t, J=2.3 Hz), 3.27 (2H, d, J=6.3 Hz), 3.93 (3H, s), 4.81 (2H, d, J=2.4 Hz), 6.14 (1H, br s), 7.03 (1H, d, J=8.3 Hz), 7.24 (1H, dd, J=8.3, 2.0 Hz), 7.47 (1H, d, J=2.0 Hz).

PRODUCTION EXAMPLE 2

According to the same method as that of Production Example 1, 1,1-dimethylpropylamine was used in place of 2,2-dimethylpropylamine to obtain N-(1,1-diemthylpropyl)-4-(2-propynyloxy)-3-methoxybenzamide (hereinafter, described as the compound 2 of the present invention) represented by the formula:

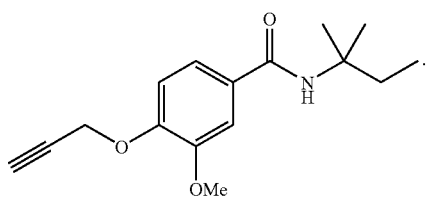

The compound 2 of the present invention:
$^1$H-NMR (CDCl$_3$) δ: 0.91 (3H, t, J=7.5 Hz), 1.42 (6H, s), 1.85 (2H, q, J=7.5 Hz), 2.52 (1H, t, J=2.4 Hz), 3.92 (3H, s), 4.80 (2H, d, J=2.4 Hz), 5.80 (1H, br s), 7.01 (1H, d, J=8.2 Hz), 7.18 (1H, dd, J=8.3, 2.1 Hz), 7.44 (1H, d, J=1.9 Hz).

PRODUCTION EXAMPLE 3

According to the same method as that of Production Example 1, 2-methylpropylamine was used in place of 2,2-dimethylpropylamine to obtain N-(i-butyl)-4-(2-propynyloxy)-3-methoxybenzamide (hereinafter, described as the compound 3 of the present invention) represented by the formula:

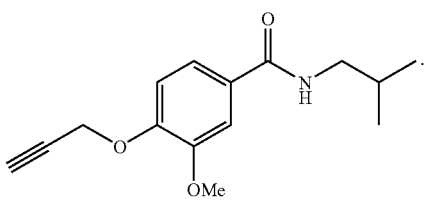

The compound 3 of the present invention:
$^1$H-NMR (CDCl$_3$) δ: 0.98 (6H, d, J=6.6 Hz), 1.84-1.95 (1H, m), 2.53 (1H, t, J=2.3 Hz), 3.28 (2H, t, J=6.3 Hz), 3.93 (3H, s), 4.81 (2H, d, J=2.4 Hz), 6.12 (1H, br s), 7.03 (1H, d, J=8.3 Hz), 7.24 (2H, dd, J=8.3, 2.0 Hz), 7.46 (1H, d, J=2.0 Hz).

PRODUCTION EXAMPLE 4

According to the same method as that of Production Example 1, 2-ethylbutylamine was used in place of 2,2-dimethylpropylamine to obtain N-(2-ethylbutyl)-4-(2-propynyloxy)-3-methoxybenzamide (hereinafter, described as the compound 4 of the present invention) represented by the formula:

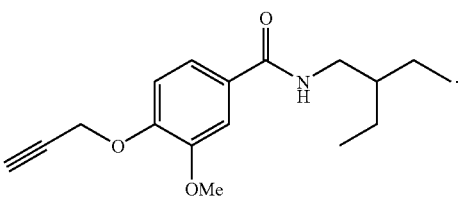

The compound 4 of the present invention:
$^1$H-NMR (CDCl$_3$) δ: 0.93 (6H, t, J=7.3 Hz), 1.33-1.55 (5H, m), 2.53 (1H, s), 3.40 (2H, t, J=6.0 Hz), 3.92 (3H, s), 4.81 (2H, d, J=2.0 Hz), 6.12 (1H, br s), 7.02 (1H, d, J=8.3 Hz), 7.20-7.31 (1H, m), 7.46 (1H, s).

PRODUCTION EXAMPLE 5

According to the same method as that of Production Example 1, 2-methylbutylamine was used in place of 2,2-dimethylpropylamine to obtain N-(2-methylbutyl)-4-(2-propynyloxy)-3-methoxybenzamide (hereinafter, described as the compound 5 of the present invention) represented by the formula:

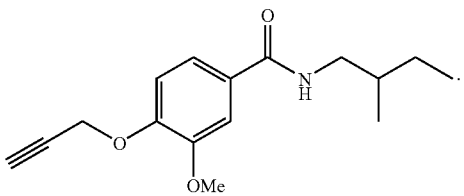

The compound 5 of the present invention:
¹H-NMR (CDCl₃) δ: 0.91-0.98 (6H, m), 1.15-1.28 (1H, m), 1.39-1.53 (1H, m), 1.61-1.74 (1H, m), 2.53 (1H, t, J=2.4 Hz), 3.20-3.45 (2H, m), 3.92 (3H, s), 4.81 (2H, d, J=2.2 Hz), 6.16 (1H, br s), 7.02 (1H, d, J=8.3 Hz), 7.24 (1H, dd, J=8.3, 2.0 Hz), 7.46 (1H, d, J=2.0 Hz).

PRODUCTION EXAMPLE 6

According to the same method as that of Production Example 1, 2-methylpentylamine was used in place of 2,2-dimethylpropylamine to obtain N-(2-methylpentyl)-4-(2-propynyloxy)-3-methoxybenzamide (hereinafter, described as the compound 6 of the present invention) represented by the formula:

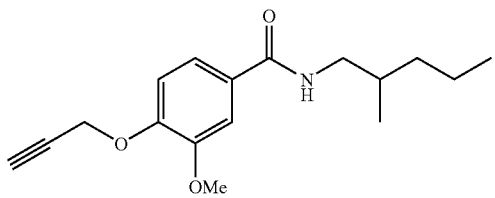

The compound 6 of the present invention:
¹H-NMR (CDCl₃) δ: 0.91 (3H, t, J=6.9 Hz), 0.95 (3H, d, J=6.8 Hz), 1.10-1.48 (4H, m), 1.69-1.82 (1H, m), 2.53 (1H, t, J=2.3 Hz), 3.20-3.43 (2H, m), 3.91 (3H, s), 4.80 (2H, d, J=2.2 Hz), 6.20 (1H, br s), 7.02 (1H, d, J=8.5 Hz), 7.25 (1H, dd, J=8.3, 2.1 Hz), 7.46 (1H, d, J=1.9 Hz).

PRODUCTION EXAMPLE 7

According to the same method as that of Production Example 1, 1-methylpropylamine was used in place of 2,2-dimethylpropylamine to obtain N-(1-methylpropyl)-4-(2-propynyloxy)-3-methoxybenzamide (hereinafter, described as the compound 7 of the present invention) represented by the formula:

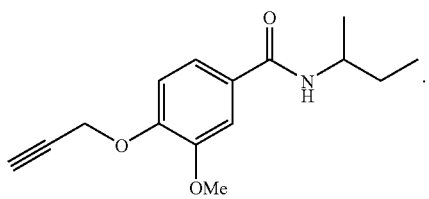

The compound 7 of the present invention:
¹H-NMR (CDCl₃) δ: 0.97 (3H, t, J=7.5 Hz), 1.23 (3H, d, J=6.5 Hz), 1.52-1.62 (2H, m), 2.52 (1H, t, J=2.4 Hz), 3.92 (3H, s), 4.05-4.17 (1H, m), 4.80 (2H, d, J=2.4 Hz), 5.89 (1H, d, J=7.5 Hz), 7.02 (1H, d, J=8.2 Hz), 7.24 (1H, dd, J=8.3, 2.1 Hz), 7.46 (1H, d, J=1.9 Hz).

PRODUCTION EXAMPLE 8

According to the same method as that of Production Example 1, 1,1-dimethylethylamine was used in place of 2,2-dimethylpropylamine to obtain N-(1,1-dimethylethyl)-4-(2-propynyloxy)-3-methoxybenzamide (hereinafter, described as the compound 8 of the present invention) represented by the formula:

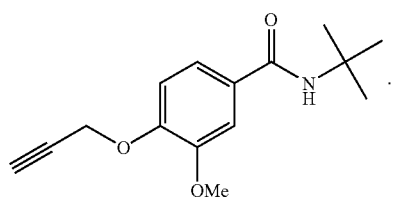

The compound 8 of the present invention:
¹H-NMR (CDCl₃) δ: 1.47 (9H, s), 2.52 (1H, t, J=2.4 Hz), 3.92 (3H, s), 4.80 (2H, d, J=2.4 Hz), 5.94 (1H, br s), 6.99 (1H, d, J=8.5 Hz), 7.18 (1H, dd, J=8.3, 2.1 Hz), 7.44 (1H, d, J=2.2 Hz).

PRODUCTION EXAMPLE 9

To a mixture of 10 ml of ethyl acetate and 0.40 g of 3-methoxy-4-(2-propynyloxy)benzoyl chloride was added 0.40 g of 1,2-dimethylpropylamine. After stirring at room temperature for 4 hours, the reaction mixture was subjected to silica gel column chromatography to obtain 0.42 g of N-(1,2-diemthylpropyl)-3-methoxy-4-(2-propynyloxy)benzamide (hereinafter, described as the compound 9 of the present invention) represented by the formula:

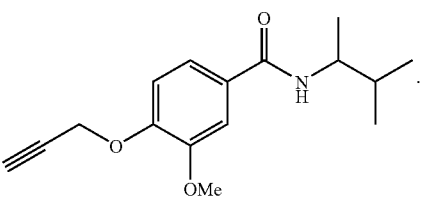

The compound 9 of the present invention:
¹H-NMR (CDCl₃) δ: 0.95 (3H, d, J=6.8 Hz), 0.97 (3H, d, J=6.8 Hz), 1.18 (3H, d, J=6.8 Hz), 1.75-1.87 (1H, m), 2.53 (1H, t, J=2.4 Hz), 3.92 (3H, s), 4.02-4.12 (1H, m), 4.81 (2H, d, J=2.4 Hz), 5.92 (1H, d, J=8.5 Hz), 7.02 (1H, d, J=8.5 Hz), 7.23 (1H, dd, J=8.3, 2.1 Hz), 7.46 (1H, d, J=1.9 Hz).

PRODUCTION EXAMPLE 10

To a mixture of 15 ml of THF and 0.35 g of 3,5-dimethoxy-4-(2-propynyloxy)benzoyl chloride were added 0.19 g of 1,2-dimethylpropylamine and 0.22 g of triethylamine. After stirring at room temperature for 2 hours, the reaction mixture was subjected to silica gel column chromatography to obtain 0.38 g of N-(1,2-diemthylpropyl)-3,5-dimethoxy-4-(2-propynyloxy)benzamide (hereinafter, described as the compound 10 of the present invention) represented by the formula:

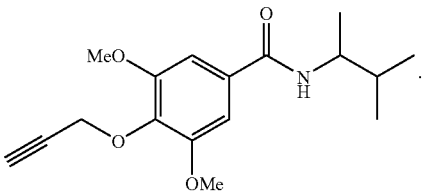

The compound 10 or the present invention:

$^1$H-NMR (CDCl$_3$) δ: 0.96 (3H, d, J=6.8 Hz), 0.98 (3H, d, J=6.8 Hz), 1.19 (3H, d, J=6.8 Hz), 1.76-1.88 (1H, m), 2.43 (1H, t, J=2.4 Hz), 3.91 (6H, s), 4.02-4.12 (1H, m), 4.77 (2H, d, J=2.4 Hz), 5.84 (1H, d, J=8.2 Hz), 6.97 (2H, s).

PRODUCTION EXAMPLE 11

A mixture of 1.0 g of 4-cyano-2-methoxyphenol, 0.6 g of 2,3-dimethyl-2-butanol and 9 ml of acetic acid was slowly added dropwise to 3 ml of concentrated sulfuric acid. The mixture obtained was stirred at room temperature for 2 hours. Water was added to the reaction mixture and the mixture was extracted with ethyl acetate. The organic layer was separated with aqueous sodium hydroxide solution and the aqueous layer obtained was acidified with dilute hydrochloric acid and extracted with ethyl acetate. The organic layer was concentrated under reduced pressure and the residue obtained was subjected to silica gel column chromatography to obtain 0.6 g of N-(1,1,2-trimethylpropyl)-4-hydroxy-3-methoxybenzamide. N-(1,1,2-trimethylpropyl)-4-hydroxy-3-methoxybenzamide:

$^1$H-NMR (CDCl$_3$) δ: 0.94 (6H, d, J=7.0 Hz), 1.39 (6H, s), 2.38-2.48 (1H, m), 3.92 (3H, s), 5.84 (1H, br s), 6.03 (1H, s), 6.89 (1H, d, J=8.2 Hz), 7.10 (1H, dd, J=8.2, 1.9 Hz), 7.44 (1H, d, J=1.9 Hz).

To 10 ml of DMF were added 0.4 g of N-(1,1,2-trimethylpropyl)-4-hydroxy-3-methoxybenzamide, 0.28 g of propargyl bromide and 0.78 g of cesium carbonate and the mixture was heated under reflux for 1 hour. Then, the reaction mixture was concentrated. Dilute hydrochloric acid was added to the residue and extracted with ethyl acetate. After the organic layer was dried over magnesium sulfate, it was concentrated under reduced pressure. The solid obtained was successively washed with hexane and methyl tert-butyl ether to obtain 0.33 g of N-(1,1,2-trimethylpropyl)-4-(2-propynyloxy)-3-methoxybenzamide (hereinafter, described as the compound 11 of the present invention) represented by the formula:

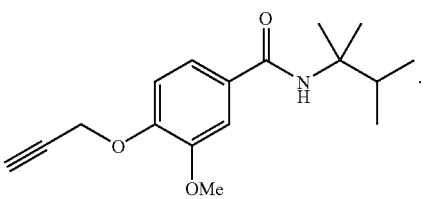

The compound 11 of the present invention:

$^1$H-NMR (CDCl$_3$) δ: 0.95 (6H, d, J=7.0 Hz), 1.40 (6H, s), 2.38-2.48 (1H, m), 2.52 (1H, t, J=2.4 Hz), 3.92 (3H, s), 4.80 (2H, d, J=2.4 Hz), 5.84 (1H, br s), 7.00 (1H, d, J=8.5 Hz), 7.17 (1H, dd, J=8.3, 2.1 Hz), 7.44 (1H, d, J=2.2 Hz).

PRODUCTION EXAMPLE 12

According to the same method as that of Production Example 1, 1-cyano-1,2-dimethylpropylamine was used in place of 2,2-dimethylpropylamine to obtain N-(1-cyano-1,2-dimethylpropyl)-4-(2-propynyloxy)-3-methoxybenzamide (hereinafter, described as the compound 12 of the present invention) represented by the formula:

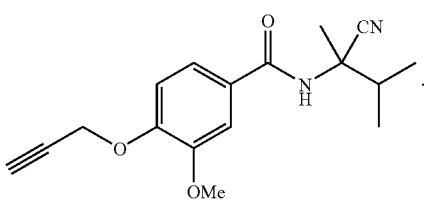

The compound 12 of the present invention:

$^1$H-NMR (CDCl$_3$) δ: 1.11 (3H, d, J=6.8 Hz), 1.20 (3H, d, J=6.8 Hz), 1.73 (3H, s), 2.47-2.55 (2H, m), 3.92 (3H, s), 4.82 (2H, d, J=2.4 Hz), 6.10 (1H, br s), 7.02 (1H, d, J=8.3 Hz), 7.21 (1H, dd, J=8.3, 2.0 Hz), 7.47 (1H, d, J=2.0 Hz).

PRODUCTION EXAMPLE 13

According to the same method as that of Production Example 1, 1,2-dimethylbutylamine was used in place of 2,2-dimethylpropylamine to obtain N-(1,2-dimethylbutyl)-4-(2-propynyloxy)-3-methoxybenzamide (hereinafter, described as the compound 13 of the present invention) represented by the formula:

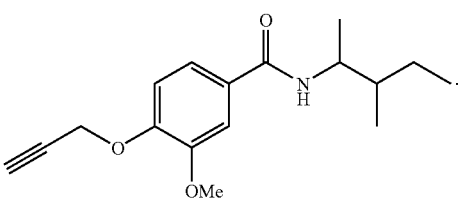

The compound 13 of the present invention:

$^1$H-NMR (CDCl$_3$) δ: 0.89-0.98 (6H, m), 1.12-1.28 (4H, m), 1.43-1.69 (2H, m), 2.52 (1H, t, J=2.4 Hz), 3.93 (3H, s), 4.09-4.27 (1H, m), 4.81 (2H, d, J=2.2 Hz), 5.92 (1H, t, J=10.7 Hz), 7.02 (1H, d, J=8.2 Hz), 7.19-7.24 (1H, m), 7.46 (1H, d, J=1.9 Hz).

PRODUCTION EXAMPLE 14

According to the same method as that of Production Example 1, 1,2,2-trimethylpropylamine was used in place of 2,2-dimethylpropylamine to obtain N-(1,2,2-trimethylpropyl)-4-(2-propynyloxy)-3-methoxybenzamide (hereinafter, described as the compound 14 of the present invention) represented by the formula:

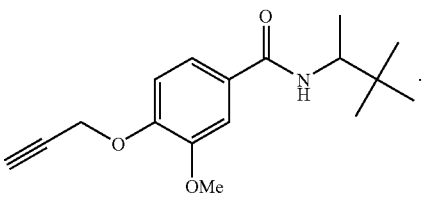

The compound 14 of the present invention:
¹H-NMR (CDCl₃) δ: 0.97 (9H, s), 1.16 (3H, d, J=6.8 Hz), 2.52 (1H, t, J=2.2 Hz), 3.93 (3H, s), 4.04-4.14 (1H, m), 4.81 (2H, d, J=2.4 Hz), 5.89 (1H, d, J=9.7 Hz), 7.03 (1H, d, J=8.2 Hz), 7.21 (1H, dd, J=8.5, 1.9 Hz), 7.47 (1H, d, J=1.9 Hz).

PRODUCTION EXAMPLE 15

According to the same method as that of Production Example 1, (1S)-1,2-dimethylpropylamine was used in place of 2,2-dimethylpropylamine to obtain N-((1S)-1,2-dimethylpropyl)-4-(2-propynyloxy)-3-methoxybenzamide (hereinafter, described as the compound 15 of the present invention) represented by the formula:

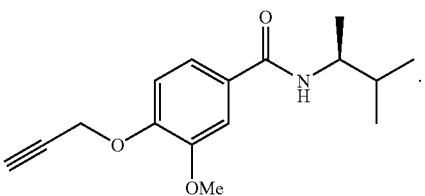

The compound 15 of the present invention:
¹H-NMR (CDCl₃) δ: 0.96 (3H, d, J=6.8 Hz), 0.98 (3H, d, J=6.8 Hz), 1.18 (3H, d, J=6.8 Hz), 1.75-1.87 (1H, m), 2.52 (1H, t, J=2.4 Hz), 3.93 (3H, s), 4.02-4.13 (1H, m), 4.81 (2H, d, J=2.4 Hz), 5.87 (1H, d, J=7.2 Hz), 7.02 (1H, d, J=8.5 Hz), 7.22 (1H, dd, J=8.2, 1.9 Hz), 7.46 (1H, d, J=1.9 Hz).

PRODUCTION EXAMPLE 16

According to the same method as that of Production Example 1, (1R)-1,2-dimethylpropylamine was used in place of 2,2-dimethylpropylamine to obtain N-((1R)-1,2-dimethylpropyl)-4-(2-propynyloxy)-3-methoxybenzamide (hereinafter, described as the compound 16 of the present invention) represented by the formula:

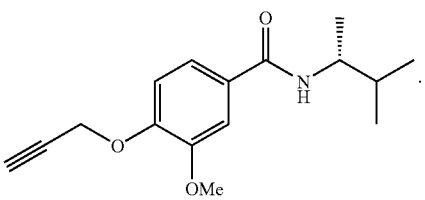

The compound 16 of the present invention:
¹H-NMR (CDCl₃) δ: 0.93-1.00 (6H, m), 1.16-1.20 (3H, m), 1.74-1.88 (1H, m), 2.50-2.54 (1H, m), 3.93 (3H, s), 4.02-4.13 (1H, m), 4.78-4.83 (2H, m), 5.87 (1H, d, J=7.7 Hz), 7.03 (1H, d, J=8.2 Hz), 7.22 (1H, d, J=8.5 Hz), 7.46 (1H, s).

PRODUCTION EXAMPLE 17

According to the same method as that of Production Example 1, (1R)-1,2,2-trimethylpropylamine was used in place of 2,2-dimethylpropylamine to obtain N-((1R)-1,2,2-trimethylpropyl)-4-(2-propynyloxy)-3-methoxybenzamide (hereinafter, described as the compound 17 of the present invention) represented by the formula:

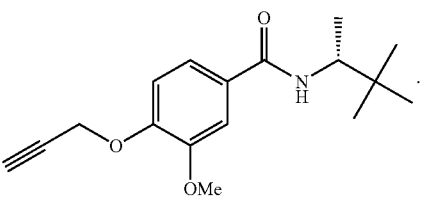

The compound 17 of the present invention:
¹H-NMR (CDCl₃) δ: 0.97 (9H, s), 1.16 (3H, d, J=6.8 Hz), 2.53 (1H, t, J=2.4 Hz), 3.93 (3H, s), 4.06-4.15 (1H, m), 4.81 (2H, d, J=2.4 Hz), 5.89 (1H, d, J=9.2 Hz), 7.03 (1H, d, J=8.5 Hz), 7.21 (1H, dd, J=8.3, 2.1 Hz), 7.47 (1H, d, J=1.9 Hz).

PRODUCTION EXAMPLE 18

According to the same method as that of Production Example 1, (1S)-1,2,2-trimethylpropylamine was used in place of 2,2-dimethylpropylamine to obtain N-((1S)-1,2,2-trimethylpropyl)-4-(2-propynyloxy)-3-methoxybenzamide (hereinafter, described as the compound 18 of the present invention) represented by the formula:

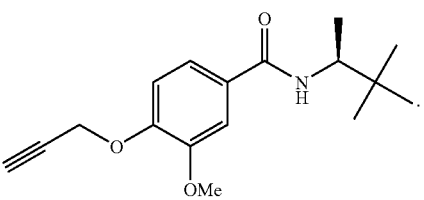

The compound 18 of the present invention:
¹H-NMR (CDCl₃) δ: 0.97 (9H, s), 1.16 (3H, d, J=6.8 Hz), 2.52 (1H, t, J=2.3 Hz), 3.94 (3H, s), 4.05-4.15 (1H, m), 4.81 (2H, d, J=2.4 Hz), 5.88 (1H, d, J=9.2 Hz), 7.03 (1H, d, J=8.2 Hz), 7.21 (1H, dd, J=8.3, 2.1 Hz), 7.47 (1H, d, J=2.2 Hz).

PRODUCTION EXAMPLE 19

According to the same method as that of Production Example 1, 1-cyano-1,2-dimethylpropylamine was used in place of 2,2-dimethylpropylamine, 4-(2-propynyloxy)-3,5-dimethoxybenzoyl chloride was used in place of 4-(2-propynyloxy)-3-methoxybenzoyl chloride to obtain N-(1-cyano-1,2-dimethylpropyl)-4-(2-propynyloxy)-3,5-dimethoxybenzamide (hereinafter, described as the compound 19 of the present invention) represented by the formula:

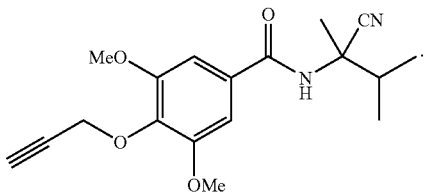

The compound 19 of the present invention:
$^1$H-NMR (CDCl$_3$) δ: 1.11 (3H, d, J=6.8 Hz), 1.20 (3H, d, J=6.8 Hz), 1.74 (3H, s), 2.44 (1H, t, J=2.4 Hz), 2.51-2.58 (1H, m), 3.90 (6H, s), 4.78 (2H, d, J=2.4 Hz), 6.10 (1H, br s), 6.96 (2H, s).

PRODUCTION EXAMPLE 20

According to the same method as that of Production Example 1, 4-(2-propynyloxy)-3,5-dimethoxybenzoyl chloride was used in place of 4-(2-propynyloxy)-3-methoxybenzoyl chloride to obtain N-(2,2-dimethylpropyl)-4-(2-propynyloxy)-3,5-dimethoxybenzamide (hereinafter, described as the compound 20 of the present invention) represented by the formula:

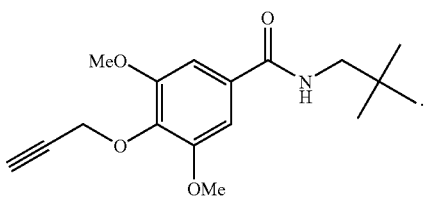

The compound 20 of the present invention:
$^1$H-NMR (CDCl$_3$) δ: 0.99 (9H, s), 2.44 (1H, t, J=2.4 Hz), 3.27 (2H, d, J=6.3 Hz), 3.91 (6H, s), 4.77 (2H, d, J=2.4 Hz), 6.13 (1H, br s), 6.99 (2H, s).

PRODUCTION EXAMPLE 21

According to the same method as that of Production Example 1, 2-methylpropylamine was used in place of 2,2-dimethylpropylamine, 4-(2-propynyloxy)-3,5-dimethoxybenzoyl chloride was used in place of 4-(2-propynyloxy)-3-methoxybenzoyl chloride to obtain N-(2-methylpropyl)-4-(2-propynyloxy)-3,5-dimethoxybenzamide (hereinafter, described as the compound 21 of the present invention) represented by the formula:

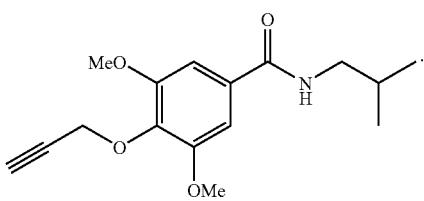

The compound 21 of the present invention:
$^1$H-NMR (CDCl$_3$) δ: 0.98 (6H, d, J=6.8 Hz), 1.85-1.97 (1H, m), 2.43 (1H, t, J=2.5 Hz), 3.28 (2H, t, J=6.5 Hz), 3.90 (6H, s), 4.77 (2H, d, J=2.4 Hz), 6.15 (1H, br s), 6.99 (2H, s).

PRODUCTION EXAMPLE 22

According to the same method as that of Production Example 1, 1,2-dimethylbutylamine was used in place of 2,2-dimethylpropylamine, 4-(2-propynyloxy)-3,5-dimethoxybenzoyl chloride was used in place of 4-(2-propynyloxy)-3-methoxybenzoyl chloride to obtain N-(1,2-dimethylbutyl)-4-(2-propynyloxy)-3,5-dimethoxybenzamide (hereinafter, described as the compound 22 of the present invention) represented by the formula:

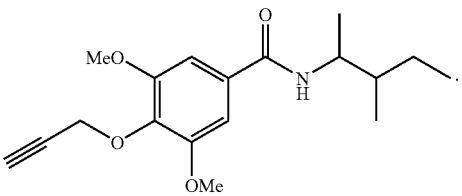

The compound 22 of the present invention:
$^1$H-NMR (CDCl$_3$) δ: 0.86-1.08 (6H, m), 1.10-1.94 (6H, m), 2.42-2.45 (1H, m), 3.85-3.96 (6H, m), 4.07-4.36 (1H, m), 4.76-4.79 (2H, m), 5.77-6.29 (1H, m), 6.94-7.02 (2H, m).

PRODUCTION EXAMPLE 23

To a mixture of 5 ml of ethyl acetate and 0.30 g of 3-fluoro-4-(2-propynyloxy)benzoyl chloride was added 0.14 g of 1,2-dimethylpropylamine. After stirring at room temperature for 3 hours, ethyl acetate was added to the reaction mixture and filtered through Celite. The filtrate was concentrated under reduced pressure and the residue was subjected to silica gel column chromatography to obtain 0.52 g of N-(1,2-diemthylpropyl)-3-fluoro-4-(2-propynyloxy)benzamide (hereinafter, described as the compound 23 of the present invention) represented by the formula:

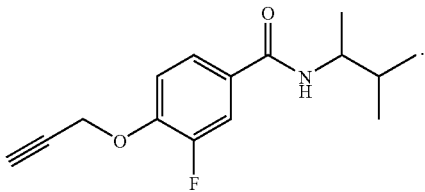

The compound 23 of the present invention:
$^1$H-NMR (CDCl$_3$) δ: 0.95 (3H, d, J=6.8 Hz), 0.97 (3H, d, J=6.8 Hz), 1.17 (3H, d, J=6.8 Hz), 1.74-1.87 (1H, m), 2.56 (1H, t, J=2.4 Hz), 4.01-4.10 (1H, m), 4.81 (2H, d, J=2.4 Hz), 5.90 (1H, d, J=8.5 Hz), 7.12 (1H, t, J=8.2 Hz), 7.47-7.57 (2H, m).

PRODUCTION EXAMPLE 24

According to the same method as that of Production Example 1, 4-(2-propynyloxy)-3-fluorobenzoyl chloride was used in place of 4-(2-propynyloxy)-3-methoxybenzoyl chloride to obtain N-(2,2-dimethylpropyl)-3-fluoro-4-(2-propynyloxy)benzamide (hereinafter, described as the compound 24 of the present invention) represented by the formula:

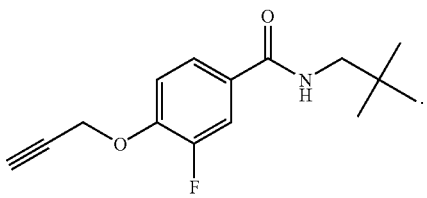

The compound 24 of the present invention:
$^1$H-NMR (CDCl$_3$) δ: 0.98 (9H, s), 2.57 (1H, t, J=2.4 Hz), 3.26 (2H, d, J=6.5 Hz), 4.82 (2H, d, J=2.4 Hz), 6.09 (1H, br s), 7.14 (1H, t, J=8.1 Hz), 7.49-7.58 (2H, m).

PRODUCTION EXAMPLE 25

According to the same method as that of Production Example 1, (1S)-1,2,2-trimethylpropylamine was used in place of 2,2-dimethylpropylamine, and 4-(2-propynyloxy)-3-fluorobenzoyl chloride was used in place of 4-(2-propynyloxy)-3-methoxybenzoyl chloride to obtain N-((1S)-1,2,2-trimethylpropyl)-3-fluoro-4-(2-propynyloxy)benzamide (hereinafter, described as the compound 25 of the present invention) represented by the formula:

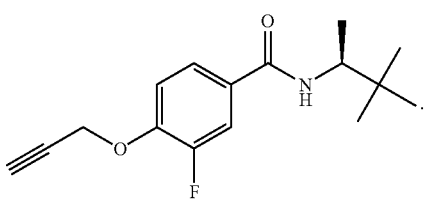

The compound 25 of the present invention:
$^1$H-NMR (CDCl$_3$) δ: 0.97 (9H, s), 1.15 (3H, d, J=6.8 Hz), 2.56 (1H, t, J=2.3 Hz), 4.02-4.13 (1H, m), 4.82 (2H, d, J=2.4 Hz), 5.84 (1H, d, J=9.2 Hz), 7.13 (1H, t, J=8.3 Hz), 7.46-7.56 (2H, m).

PRODUCTION EXAMPLE 26

According to the same method as that of Production Example 1, 1,2-dimethylbutylamine was used in place of 2,2-dimethylpropylamine, and 4-(2-propynyloxy)-3-fluorobenzoyl chloride was used in place of 4-(2-propynyloxy)-3-methoxybenzoyl chloride to obtain N-(1,2-dimethylbutyl)-3-fluoro-4-(2-propynyloxy)benzamide (hereinafter, described as the compound 26 of the present invention) represented by the formula:

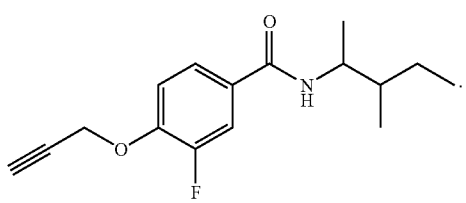

The compound 26 of the present invention:
$^1$H-NMR (CDCl$_3$) δ: 0.84-1.30 (10H, m), 1.40-1.94 (2H, m), 2.57 (1H, t, J=2.4 Hz), 3.68-4.25 (1H, m), 4.79-4.84 (2H, m), 5.85-6.35 (1H, m), 7.08-7.17 (1H, m), 7.48-7.61 (2H, m).

PRODUCTION EXAMPLE 27

According to the same method as that of Production Example 1, 1-cyano-1,2-dimethylpropylamine was used in place of 2,2-dimethylpropylamine, and 4-(2-propynyloxy)-3-fluorobenzoyl chloride was used in place of 4-(2-propynyloxy)-3-methoxybenzoyl chloride to obtain N-(1-cyano-1,2-dimethylpropyl)-3-fluoro-4-(2-propynyloxy)benzamide (hereinafter, described as the compound 27 of the present invention) represented by the formula:

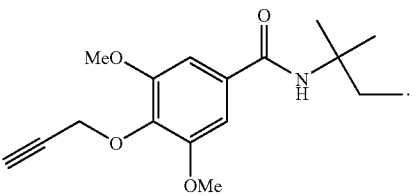

The compound 27 of the present invention:
$^1$H-NMR (CDCl$_3$) δ: 1.11 (3H, d, J=6.8 Hz), 1.20 (3H, d, J=6.8 Hz), 1.73 (3H, s), 2.44-2.56 (1H, m), 2.57 (1H, t, J=2.4 Hz), 4.83 (2H, d, J=2.4 Hz), 6.03 (1H, br s), 7.15 (1H, t, J=8.5 Hz), 7.48-7.58 (2H, m).

PRODUCTION EXAMPLE 28

According to the same method as that of Production Example 1, 1,1-dimethylpropylamine was used in place of 2,2-dimethylpropylamine to obtain N-(1,1-dimethylpropyl)-3,5-dimethoxy-4-(2-propynyloxy)benzamide (hereinafter, described as the compound 28 of the present invention) represented by the formula:

The compound 28 of the present invention:
$^1$H-NMR (CDCl$_3$) δ: 0.91 (3H, t, J=7.5 Hz), 1.42 (6H, s), 1.86 (2H, q, J=7.5 Hz), 2.43 (1H, t, J=2.4 Hz), 3.90 (6H, s), 4.76 (2H, d, J=2.4 Hz), 5.75 (1H, br s), 6.94 (2H, s).

PRODUCTION EXAMPLE 29

According to the same method as that of Production Example 1, 1-methylethylamine was used in place of 2,2-dimethylpropylamine to obtain N-(1-methylethyl)-3-methoxy-4-(2-propynyloxy)benzamide (hereinafter, described as the compound 29 of the present invention) represented by the formula:

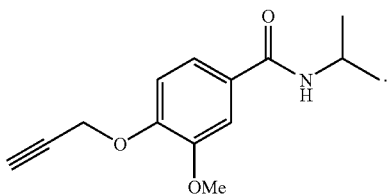

The compound 29 of the present invention:
$^1$H-NMR (CDCl$_3$) δ: 1.25 (6H, d, J=6.5 Hz), 2.53 (1H, t, J=2.4 Hz), 3.91 (3H, s), 4.20-4.34 (1H, m), 4.80 (2H, d, J=2.4 Hz), 6.01-6.03 (1H, br m), 7.00 (1H, d, J=8.4 Hz), 7.25 (1H, dd, J=8.4, 2.0 Hz), 7.45 (1H, d, J=2.0 Hz).

PRODUCTION EXAMPLE 30

According to the same method as that of Production Example 10, (1S)-1,2-dimethylpropylamine was used in place of 1,2-dimethylpropylamine to obtain N-((1S)-1,2-dimethylpropyl)-3,5-dimethoxy-4-(2-propynyloxy)benzamide (hereinafter, described as the compound 30 of the present invention) represented by the formula:

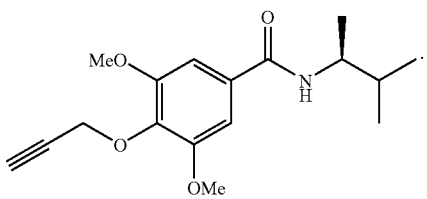

The compound 30 of the present invention:
$^1$H-NMR (CDCl$_3$) δ: 0.97 (3H, d, J=6.8 Hz), 0.98 (3H, d, J=6.8 Hz), 1.19 (3H, d, J=6.8 Hz), 1.76-1.88 (1H, m), 2.43 (1H, t, J=2.4 Hz), 3.91 (6H, s), 4.01-4.13 (1H, m), 4.77 (2H, d, J=2.4 Hz), 5.84 (1H, d, J=8.7 Hz), 6.97 (2H, s).

PRODUCTION EXAMPLE 31

According to the same method as that of Production Example 23, (1S)-1,2-dimethylpropylamine was used in place of 1,2-dimethylpropylamine to obtain N-((1S)-1,2-dimethylpropyl)-3-fluoro-4-(2-propynyloxy)benzamide (hereinafter, described as the compound 31 of the present invention) represented by the formula:

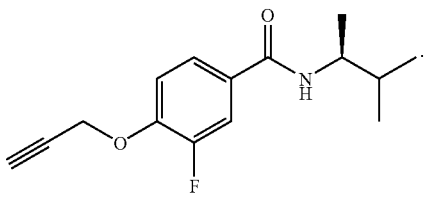

The compound 31 of the present invention:
$^1$H-NMR (CDCl$_3$) δ: 0.95 (3H, d, J=6.8 Hz), 0.97 (3H, d, J=6.8 Hz), 1.17 (3H, d, J=6.8 Hz), 1.74-1.87 (1H, m), 2.56 (1H, t, J=2.4 Hz), 4.00-4.12 (1H, m), 4.81 (2H, d, J=2.4 Hz), 5.83-5.85 (1H, br m), 7.10-7.15 (1H, m), 7.49-7.56 (2H, m).

PRODUCTION EXAMPLE 32

According to the same method as that of Production Example 10, 1,1,2-trimethylpropylamine was used in place of 1,2-dimethylpropylamine to obtain N-(1,1,2-trimethylpropyl)-3,5-dimethoxy-4-(2-propynyloxy)benzamide (hereinafter, described as the compound 32 of the present invention) represented by the formula:

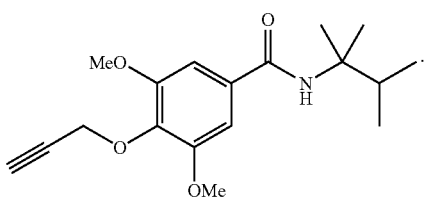

The compound 32 of the present invention:
$^1$H-NMR (CDCl$_3$) δ: 0.95 (6H, d, J=7.0 Hz), 1.40 (6H, s), 2.41-2.48 (1H, m), 2.43 (1H, t, J=2.4 Hz), 3.89 (6H, d, J=11.1 Hz), 4.76 (2H, d, J=2.4 Hz), 5.79 (1H, s), 6.93 (2H, s).

PRODUCTION EXAMPLE 33

According to the same method as that of Production Example 23, 1,1,2-trimethylpropylamine was used in place of 1,2-dimethylpropylamine to obtain N-(1,1,2-trimethylpropyl)-3-fluoro-4-(2-propynyloxy)benzamide (hereinafter, described as the compound 33 of the present invention) represented by the formula:

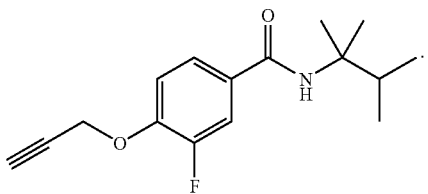

The compound 33 of the present invention:
$^1$H-NMR (CDCl$_3$) δ: 0.94 (6H, d, J=7.0 Hz), 1.38 (6H, s), 2.38-2.45 (1H, m), 2.55 (1H, t, J=2.4 Hz), 4.81 (2H, d, J=2.4 Hz), 5.76 (1H, s), 7.11 (1H, t, J=8.2 Hz), 7.44-7.51 (2H, m).

PRODUCTION EXAMPLE 34

According to the same method as that of Production Example 10, (1S)-1,2,2-trimethylpropylamine was used in place of 1,2-dimethylpropylamine to obtain N-((1S)-1,2,2-trimethylpropyl)-3,5-dimethoxy-4-(2-propynyloxy)benzamide (hereinafter, described as the compound 34 of the present invention) represented by the formula:

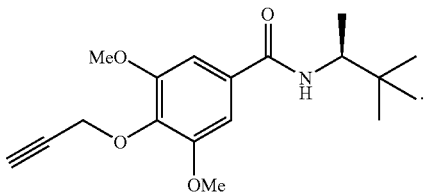

The compound 34 of the present invention:
$^1$H-NMR (CDCl$_3$) δ: 0.98 (9H, s), 1.17 (3H, d, J=6.8 Hz), 2.44 (1H, t, J=2.4 Hz), 3.91 (6H, s), 4.05-4.14 (1H, m), 4.77 (2H, d, J=2.4 Hz), 5.86 (1H, d, J=9.4 Hz), 6.97 (2H, s).

PRODUCTION EXAMPLE 35

To 20 ml of toluene were added 0.80 g of N-((1S)-1,2-dimethylpropyl)-3-methoxy-4-(2-propynyloxy)benzamide and 1.2 g of Lawesson's reagent, and the mixture was heated under reflux for 2 hours. The reaction mixture was subjected to silica gel column chromatography as it was to obtain 0.78 g of N-((1S)-1,2-diemthylpropyl)-3-methoxy-4-(2-propynyloxy)benzthioamide (hereinafter, described as the compound 35 of the present invention) represented by the formula:

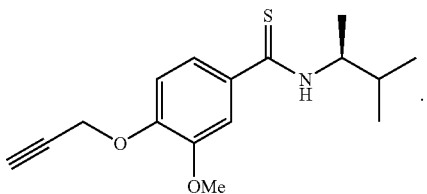

The compound 35 of the present invention:
$^1$H-NMR (CDCl$_3$) δ: 1.00 (3H, d, J=6.8 Hz), 1.03 (3H, d, J=6.8 Hz), 1.27 (3H, d, J=6.8 Hz), 1.97-2.09 (1H, m), 2.52 (1H, t, J=2.4 Hz), 3.93 (3H, s), 4.61-4.72 (1H, m), 4.80 (2H, d, J=2.4 Hz), 6.98 (1H, d, J=8.5 Hz), 7.13 (1H, dd, J=8.5, 2.2 Hz), 7.37 (1H, d, J=7.7 Hz), 7.53 (1H, d, J=1.9 Hz).

PRODUCTION EXAMPLE 36

According to the same method as that of Production Example 1, 1-ethylpropylamine was used in place of 2,2-dimethylpropylamine to obtain N-(1-ethylpropyl)-3-methoxy-4-(2-propynyloxy)benzamide (hereinafter, described as the compound 36 of the present invention) represented by the formula:

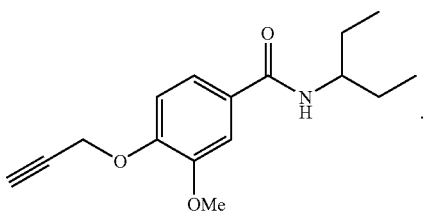

The compound 36 of the present invention:
$^1$H-NMR (CDCl$_3$) δ: 0.96 (6H, t, J=7.4 Hz), 1.42-1.55 (2H, m), 1.60-1.72 (2H, m), 2.52 (1H, t, J=2.4 Hz), 3.93 (3H, s), 3.95-4.05 (1H, m), 4.81 (2H, d, J=2.2 Hz), 5.75 (1H, d, J=8.5 Hz), 7.03 (1H, d, J=8.2 Hz), 7.23 (1H, dd, J=8.3, 2.1 Hz), 7.47 (1H, d, J=2.2 Hz).

PRODUCTION EXAMPLE 37

According to the same method as that of Production Example 23, 2-methylpropylamine was used in place of 1,2-dimethylpropylamine to obtain N-(2-methylpropyl)-3-fluoro-4-(2-propynyloxy)benzamide (hereinafter, described as the compound 37 of the present invention) represented by the formula:

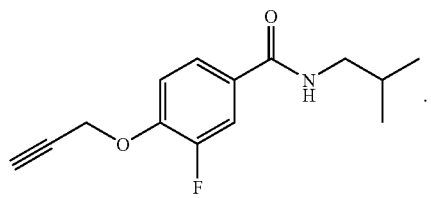

The compound 37 of the present invention:
$^1$H-NMR (CDCl$_3$) δ: 0.98 (6H, d, J=6.8 Hz), 1.84-1.94 (1H, m), 2.56 (1H, t, J=2.4 Hz), 3.28 (2H, t, J=6.5 Hz), 4.82 (2H, d, J=2.4 Hz), 6.03 (1H, br s), 7.13 (1H, t, J=8.3 Hz), 7.50-7.56 (2H, m).

PRODUCTION EXAMPLE 38

A mixture of 346 mg of 3,5-difluoro-4-(2-propynyloxy)benzoyl chloride and 1 ml of tetrahydroduran was added dropwise under ice cooling to a mixture of 5 ml of tetrahydroduran, 131 mg of (1S)-1,2-dimethylpropylamine and 182 mg of triethylamine. Then, the mixture obtained was stirred at room temperature for 0.5 hour. The reaction mixture was filtered and the filtrate was concentrated under reduced pressure. Water was added to the residue and it was extracted with ethyl acetate. The organic layer was dried over anhydrous magnesium sulfate and concentrated under reduced pressure to obtain 344 mg of N-((1S)-1,2-dimemthylpropyl)-3,5-difluoro-4-(2-propynyloxy)benzamide (hereinafter, described as the compound 38 of the present invention) represented by the formula:

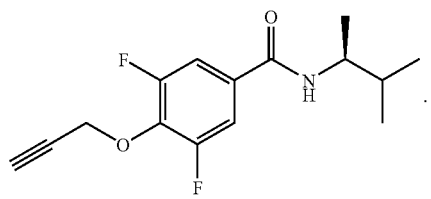

The compound 38 of the present invention:
$^1$H-NMR (CDCl$_3$) δ: 0.96 (3H, d, J=6.6 Hz), 0.97 (3H, d, J=6.8 Hz), 1.18 (3H, d, J=6.8 Hz), 1.74-1.86 (1H, m), 2.51 (1H, t, J=2.4 Hz), 3.99-4.09 (1H, m), 4.87 (2H, d, J=2.4 Hz), 5.80 (1H, d, J=7.6 Hz), 7.30-7.39 (2H, m).

PRODUCTION EXAMPLE 39

A mixture of 346 mg of 3,5-difluoro-4-(2-propynyloxy)benzoyl chloride and 1 ml of tetrahydrofuran was added dropwise under ice cooling to a mixture of 5 ml of tetrahydrofuran, 131 mg of 1,2-dimethylpropylamine and 182 mg of triethylamine. The mixture obtained was stirred at room temperature for 0.5 hour. The reaction mixture was filtered and the filtrate was concentrated under reduced pressure. Water was added to the residue and it was extracted with ethyl acetate. The organic layer was dried over anhydrous magnesium sulfate and concentrated under reduced pressure to obtain 342 mg of N-(1,2-dimemthylpropyl)-3,5-difluoro-4-(2-propynyloxy)benzamide (hereinafter, described as the compound 39 of the present invention) represented by the formula:

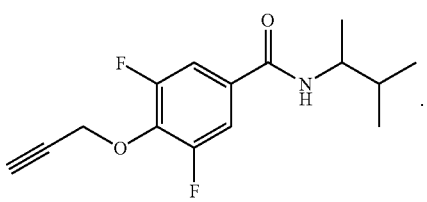

The compound 39 of the present invention:
$^1$H-NMR (CDCl$_3$) δ: 0.96 (3H, d, J=6.8 Hz), 0.97 (3H, d, J=6.8 Hz), 1.18 (3H, d, J=6.8 Hz), 1.76-1.86 (1H, m), 2.51 (1H, t, J=2.4 Hz), 4.00-4.10 (1H, m), 4.87 (2H, d, J=2.4 Hz), 5.80 (1H, d, J=7.3 Hz), 7.30-7.37 (2H, m).

PRODUCTION EXAMPLE 40

According to the same method as that of Production Example 39, 1,1,2-trimethylpropylamine was used in place of 1,2-dimethylpropylamine to obtain N-(1,1,2-trimethylpropyl)-3,5-difluoro-4-(2-propynyloxy)benzamide (hereinafter, described as the compound 40 of the present invention) represented by the formula:

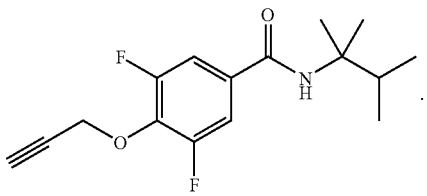

The compound 40 of the present invention:
$^1$H-NMR (CDCl$_3$) δ: 0.94 (6H, d, J=6.8 Hz), 1.38 (6H, s), 2.37-2.43 (1H, m), 2.51 (1H, t, J=2.4 Hz), 4.86 (2H, d, J=2.4 Hz), 5.73 (1H, br s), 7.25-7.31 (2H, m).

PRODUCTION EXAMPLE 41

According to the same method as that of Production Example 39, (1S)-1,2,2-trimethylpropylamine was used in place of 1,2-dimethylpropylamine to obtain N-((1S)-1,2,2-trimethylpropyl)-3,5-difluoro-4-(2-propynyloxy)benzamide (hereinafter, described as the compound 41 of the present invention) represented by the formula:

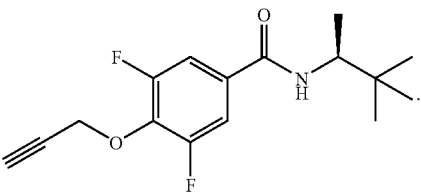

The compound 41 of the present invention:
$^1$H-NMR (CDCl$_3$) δ: 0.97 (9H, s), 1.16 (3H, d, J=6.8 Hz), 2.52 (1H, t, J=2.4 Hz), 4.02-4.14 (1H, m), 4.88 (2H, d, J=2.4 Hz), 5.79 (1H, d, J=8.8 Hz), 7.29-7.37 (2H, m).

PRODUCTION EXAMPLE 42

According to the same method as that of Production Example 39, 2-methylpropylamine was used in place of 1,2-dimethylpropylamine to obtain N-(2-methylpropyl)-3,5-difluoro-4-(2-propynyloxy)benzamide (hereinafter, described as the compound 42 of the present invention) represented by the formula:

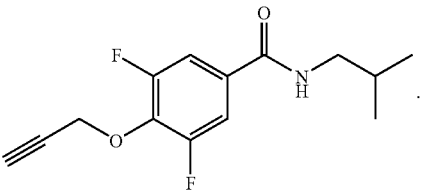

The compound 42 of the present invention:
$^1$H-NMR (CDCl$_3$) δ: 0.98 (6H, d, J=6.8 Hz), 1.86-1.93 (1H, m), 2.51 (1H, t, J=2.4 Hz), 3.27 (2H, t, J=6.5 Hz), 4.88 (2H, d, J=2.4 Hz), 6.08 (1H, br s), 7.31-7.39 (2H, m).

PRODUCTION EXAMPLE 43

A mixture of 200 mg of 3-fluoro-5-methoxy-4-(2-propynyloxy)benzoyl chloride and 1 ml of tetrahydrofuran was added dropwise under ice cooling to a mixture of 5 ml of tetrahydrofuran, 72 mg of 1,2-dimethylpropylamine and 100 mg of triethylamine. The mixture obtained was stirred at room temperature for 0.5 hour. The reaction mixture was filtered and the filtrate was concentrated under reduced pressure. Water was added to the residue and it was extracted with chloroform. The organic layer was dried over anhydrous magnesium sulfate and concentrated under reduced pressure to obtain 197 mg of N-(1,2-dimemthylpropyl)-3-fluoro-5-methoxy-4-(2-propynyloxy)benzamide (hereinafter, described as the compound 43 of the present invention) represented by the formula:

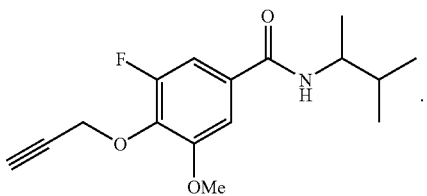

The compound 43 of the present invention:
¹H-NMR (CDCl₃) δ: 0.96 (3H, d, J=6.8 Hz), 0.97 (3H, d, J=6.8 Hz), 1.18 (3H, d, J=6.8 Hz), 1.76-1.86 (1H, m), 2.47 (1H, t, J=2.4 Hz), 3.93 (3H, s), 4.02-4.10 (1H, m), 4.83 (2H, d, J=2.4 Hz), 5.80 (1H, d, J=8.2 Hz), 7.01 (1H, dd, J=10.1, 1.9 Hz), 7.25-7.26 (1H, m).

PRODUCTION EXAMPLE 44

According to the same method as that of Production Example 43, (1S)-1,2-dimethylpropylamine was used in place of 1,2-dimethylpropylamine to obtain N-((1S)-1,2-dimethylpropyl)-3-fluoro-5-methoxy-4-(2-propynyloxy)benzamide (hereinafter, described as the compound 44 of the present invention) represented by the formula:

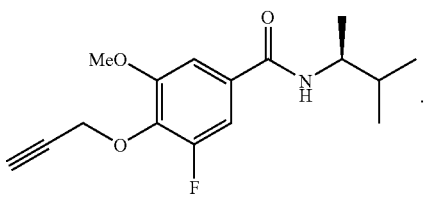

The compound 44 of the present invention:
¹H-NMR (CDCl₃) δ: 0.96 (3H, d, J=4.1 Hz), 0.97 (3H, d, J=4.3 Hz), 1.18 (3H, d, J=6.8 Hz), 1.74-1.88 (1H, m), 2.47 (1H, t, J=2.3 Hz), 3.93 (3H, s), 4.00-4.13 (1H, m), 4.82 (2H, d, J=2.3 Hz), 5.87 (1H, d, J=8.0 Hz), 7.03 (1H, d, J=10.1 Hz), 7.23-7.28 (1H, m).

PRODUCTION EXAMPLE 45

According to the same method as that of Production Example 43, (1S)-1,2,2-trimethylpropylamine was used in place of 1,2-dimethylpropylamine to obtain N-((1S)-1,2,2-trimethylpropyl)-3-fluoro-5-methoxy-4-(2-propynyloxy)benzamide (hereinafter, described as the compound 45 of the present invention) represented by the formula:

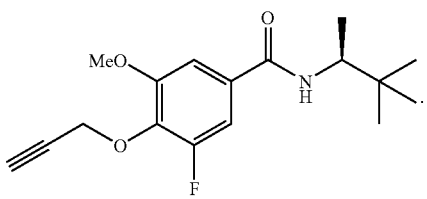

The compound 45 of the present invention:
¹H-NMR (CDCl₃) δ: 0.97 (9H, s), 1.16 (3H, d, J=6.8 Hz), 2.47 (1H, t, J=2.4 Hz), 3.93 (3H, s), 4.03-4.12 (1H, m), 4.83 (2H, d, J=2.4 Hz), 5.83 (1H, d, J=8.9 Hz), 7.00 (1H, dd, J=10.4, 1.9 Hz), 7.24-7.27 (1H, m).

PRODUCTION EXAMPLE 46

According to the same method as that of Production Example 43, 1,1,2-trimethylpropylamine was used in place of 1,2-dimethylpropylamine to obtain N-(1,1,2-trimethylpropyl)-3-fluoro-5-methoxy-4-(2-propynyloxy)benzamide (hereinafter, described as the compound 46 of the present invention) represented by the formula:

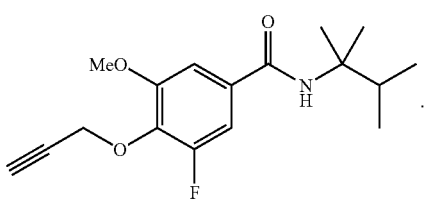

The compound 46 of the present invention:
¹H-NMR (CDCl₃) δ: 0.95 (6H, d, J=6.8 Hz), 1.39 (6H, s), 2.35-2.46 (1H, m), 2.46 (1H, t, J=2.4 Hz), 3.92 (3H, s), 4.82 (2H, d, J=2.4 Hz), 5.76 (1H, br s), 6.96 (1H, dd, J=10.1, 1.9 Hz), 7.21-7.24 (1H, m).

PRODUCTION EXAMPLE 47

According to the same method as that of Production Example 39, 1-methylethylamine was used in place of 1,2-dimethylpropylamine to obtain N-(1-methylethyl)-3,5-difluoro-4-(2-propynyloxy)benzamide (hereinafter, described as the compound 47 of the present invention) represented by the formula:

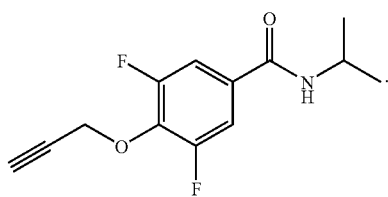

The compound 47 of the present invention:
¹H-NMR (CDCl₃) δ: 1.26 (6H, d, J=6.5 Hz), 2.51 (1H, t, J=2.4 Hz), 4.19-4.31 (1H, m), 4.87 (2H, d, J=2.4 Hz), 5.82 (1H, br s), 7.31-7.37 (2H, m).

PRODUCTION EXAMPLE 48

According to the same method as that of Production Example 39, 1-ethylpropylamine was used in place of 1,2-dimethylpropylamine to obtain N-(1-ethylpropyl)-3,5-difluoro-4-(2-propynyloxy)benzamide (hereinafter, described as the compound 48 of the present invention) represented by the formula:

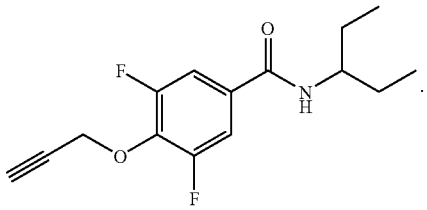

The compound 48 of the present invention:
¹H-NMR (CDCl₃) δ: 0.95 (6H, t, J=7.5 Hz), 1.43-1.54 (2H, m), 1.61-1.71 (2H, m), 2.51 (1H, t, J=2.4 Hz), 3.93-4.02 (1H, m), 4.88 (2H, d, J=2.4 Hz), 5.66 (1H, d, J=8.2 Hz), 7.31-7.38 (2H, m).

PRODUCTION EXAMPLE 49

According to the same method as that of Production Example 1, (1S)-1,2-dimethylpropylamine was used in place of 2,2-dimethylpropylamine, 3-fluoro-5-methoxy-4-(2-propynyloxy)benzoyl chloride was used in place of 4-(2-propynyloxy)-3-methoxybenzoyl chloride to obtain N-((1S)-1,2-dimethylpropyl)-3-fluoro-5-methoxy-4-(2-propynyloxy)benzamide (hereinafter, described as the compound 49 of the present invention) represented by the formula:

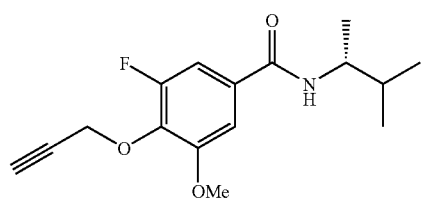

was obtained.

The compound 49 of the present invention:
¹H-NMR (CDCl₃) δ: 0.96 (3H, d, J=6.8 Hz), 0.97 (3H, d, J=6.8 Hz), 1.18 (3H, d, J=6.8 Hz), 1.75-1.87 (1H, m), 2.47 (1H, t, J=2.4 Hz), 3.93 (3H, s), 3.99-4.12 (1H, m), 4.83 (2H, d, J=2.4 Hz), 5.85 (1H, d, J=8.5 Hz), 7.02 (1H, dd, J=10.1, 1.9 Hz), 7.25 (1H, t, J=1.7 Hz).

PRODUCTION EXAMPLE 50

According to the same method as that of Production Example 1, 3,5-difluoro-4-(2-propynyloxy)benzoyl chloride was used in place of 4-(2-propynyloxy)-3-methoxybenzoyl chloride to obtain N-(2,2-dimethylpropyl)-3,5-difluoro-4-(2-propynyloxy)benzamide (hereinafter, described as the compound 50 of the present invention) represented by the formula:

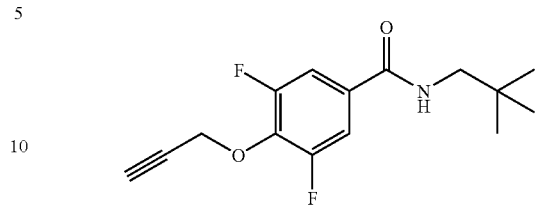

was obtained.

The compound 50 of the present invention:
¹H-NMR (CDCl₃) δ: 0.97 (9H, s), 2.53 (1H, t, J=2.4 Hz), 3.24 (2H, d, J=6.5 Hz), 4.87 (2H, d, J=2.4 Hz), 6.35 (1H, br s), 7.33-7.40 (2H, m).

PRODUCTION EXAMPLE 51

According to the same method as that of Production Example 1, 1,1-dimethyl-2-propynylamine was used in place of 2,2-dimethylpropylamine, 3,5-difluoro-4-(2-propynyloxy)benzoyl chloride was used in place of 4-(2-propynyloxy)-3-methoxybenzoyl chloride to obtain N-(1,1-dimethyl-2-propynyl)-3,5-difluoro-4-(2-propynyloxy)benzamide (hereinafter, described as the compound 51 of the present invention) represented by the formula:

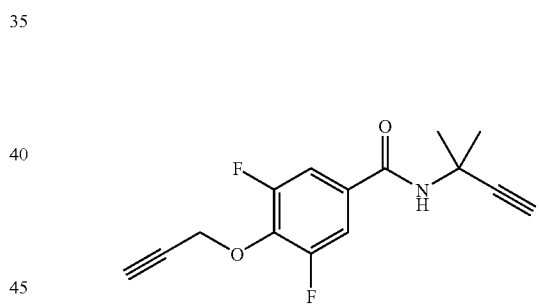

was obtained.

The compound 51 of the present invention:
¹H-NMR (CDCl₃) δ: 1.75 (6H, s), 2.40 (1H, s), 2.50-2.53 (1H, m), 4.88 (2H, d, J=2.2 Hz), 6.09 (1H, br s), 7.31-7.38 (2H, m).

PRODUCTION EXAMPLE 52

According to the same method as that of Production Example 1, 1,1-diethyl-2-propynylamine was used in place of 2,2-dimethylpropylamine, 3,5-difluoro-4-(2-propynyloxy)benzoyl chloride was used in place of 4-(2-propynyloxy)-3-methoxybenzoyl chloride to obtain N-(1,1-diethyl-2-propynyl)-3,5-difluoro-4-(2-propynyloxy)benzamide (hereinafter, described as the compound 52 of the present invention) represented by the formula:

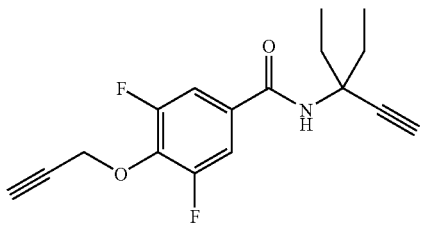

was obtained.

The compound 52 of the present invention:
$^1$H-NMR (CDCl$_3$) δ: 1.03 (6H, t, J=7.5 Hz), 1.84-1.95 (2H, m), 2.24-2.35 (2H, m), 2.43 (1H, s), 2.52 (1H, t, J=2.4 Hz), 4.88 (2H, d, J=2.4 Hz), 5.96 (1H, br s), 7.30-7.36 (2H, m).

PRODUCTION EXAMPLE 53

According to the same method as that of Production Example 1, 1,2-dimethyl-1-cyanopropylamine was used in place of 2,2-dimethylpropylamine, 3,5-difluoro-4-(2-propynyloxy)benzoyl chloride was used in place of 4-(2-propynyloxy)-3-methoxybenzoyl chloride to obtain N-(1,2-dimethyl-1-cyanopropyl)-3,5-difluoro-4-(2-propynyloxy)benzamide (hereinafter, described as the compound 53 of the present invention) represented by the formula:

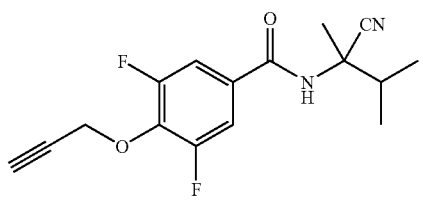

was obtained.

The compound 53 of the present invention:
$^1$H-NMR (CDCl$_3$) δ: 1.10 (3H, d, J=7.0 Hz), 1.20 (3H, d, J=6.8 Hz), 1.73 (3H, s), 2.45-2.53 (1H, m), 2.52 (1H, t, J=2.4 Hz), 4.89 (2H, d, J=2.4 Hz), 6.09 (1H, br s), 7.31-7.39 (2H, m).

PRODUCTION EXAMPLE 54

According to the same method as that of Production Example 1, 1-ethoxycarbonyl-1-methyl)ethylamine was used in place of 2,2-dimethylpropylamine, 3,5-difluoro-4-(2-propynyloxy)benzoyl chloride was used in place of 4-(2-propynyloxy)-3-methoxybenzoyl chloride to obtain N-(1-ethoxycarbonyl-1-methyl)ethyl-3,5-difluoro-4-(2-propynyloxy)benzamide (hereinafter, described as the compound 54 of the present invention) represented by the formula:

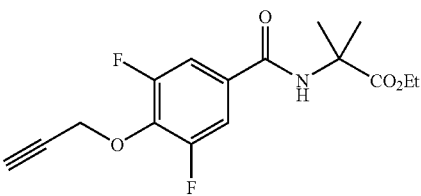

was obtained.

The compound 53 of the present invention:
$^1$H-NMR (CDCl$_3$) δ: 1.30 (3H, t, J=7.1 Hz), 1.68 (6H, s), 2.52 (1H, t, J=2.4 Hz), 4.25 (2H, q, J=7.1 Hz), 4.88 (2H, d, J=2.4 Hz), 6.81 (1H, br s), 7.32-7.40 (2H, m).

PRODUCTION EXAMPLE 55

According to the same method as that of Production Example 1, 1-methylbutylamine was used in place of 2,2-dimethylpropylamine to obtain N-(1-methylbutyl)-3-methoxy-4-(2-propynyloxy)benzamide (hereinafter, described as the compound 55 of the present invention) represented by the formula:

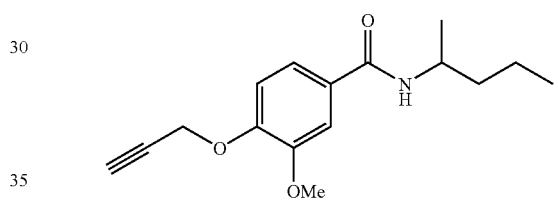

was obtained.

The compound 55 of the present invention:
$^1$H-NMR (CDCl$_3$) δ: 0.93 (3H, t, J=7.1 Hz), 1.22 (3H, d, J=6.5 Hz), 1.35-1.59 (4H, m), 2.53 (1H, t, J=2.4 Hz), 3.90 (3H, s), 4.15-4.22 (1H, m), 4.79 (2H, d, J=2.2 Hz), 6.08 (1H, d, J=8.2 Hz), 7.00 (1H, d, J=8.2 Hz), 7.26 (1H, dd, J=8.2, 1.9 Hz), 7.46 (1H, d, J=1.9 Hz).

PRODUCTION EXAMPLE 56

According to the same method as that of Production Example 1, 1-methylbutylamine was used in place of 2,2-dimethylpropylamine, 3,5-dimethoxy-4-(2-propynyloxy)benzoyl chloride was used in place of 4-(2-propynyloxy)-3-methoxybenzoyl chloride to obtain N-(1-methylbutyl)-3,5-dimethoxy-4-(2-propynyloxy)benzamide (hereinafter, described as the compound 56 of the present invention) represented by the formula:

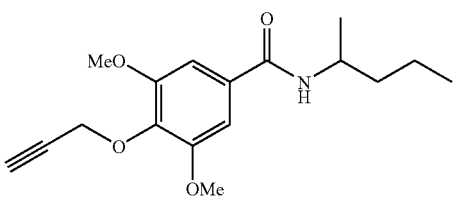

was obtained.

The compound 56 of the present invention:

¹H-NMR (CDCl₃) δ: 0.93 (3H, t, J=7.2 Hz), 1.22 (3H, d, J=6.8 Hz), 1.35-1.60 (4H, m), 2.44 (1H, t, J=2.4 Hz), 3.88 (6H, s), 4.14-4.22 (1H, m), 4.75 (2H, d, J=2.4 Hz), 6.14 (1H, d, J=8.3 Hz), 7.01 (2H, s).

PRODUCTION EXAMPLE 57

According to the same method as that of Production Example 1, 1-methylbutylamine was used in place of 2,2-dimethylpropylamine, 3-fluoro-4-(2-propynyloxy)benzoyl chloride was used in place of 4-(2-propynyloxy)-3-methoxybenzoyl chloride to obtain N-(1-methylbutyl)-3-fluoro-4-(2-propynyloxy)benzamide (hereinafter, described as the compound 57 of the present invention) represented by the formula:

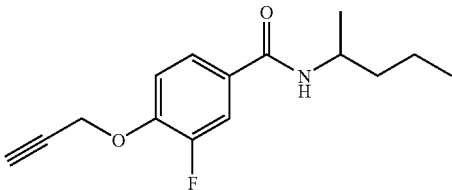

was obtained.

The compound 57 of the present invention:

¹H-NMR (CDCl₃) δ: 0.93 (3H, t, J=7.2 Hz), 1.22 (3H, d, J=6.6 Hz), 1.35-1.55 (4H, m), 2.56 (1H, t, J=2.3 Hz), 4.14-4.21 (1H, m), 4.81 (2H, d, J=2.4 Hz), 5.88 (1H, d, J=8.0 Hz), 7.11 (1H, t, J=8.3 Hz), 7.49-7.56 (2H, m).

Then, the production of the production intermediates of the compounds of the present invention will be illustrated by Reference Production Examples.

REFERENCE PRODUCTION EXAMPLE 1

To 100 ml of DMF were added 11.8 g of 4-hydroxy-3,5-dimethoxybenzoic acid, 15.7 g of propargyl bromide and 18 g of potassium carbonate, and the mixture obtained was stirred at room temperature for 8 hours and at 80° C. for 4 hours. Then, ethyl acetate was added to the reaction mixture and the mixture was filtered through Celite. Water and dilute hydrochloric acid were added to the filtrate in order and it was extracted with ethyl acetate. The organic layer was dried over magnesium sulfate and concentrated under reduced pressure. The crystals obtained were washed with a mix solvent of hexane and MTBE to obtain 15.5 g of 2-propynyl 4-(2-propynyloxy)-3,5-dimethoxybenzoate represented by the formula:

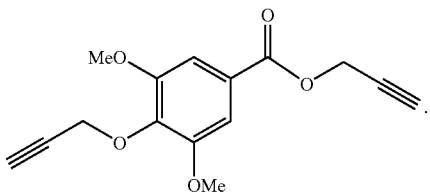

2-Propynyl 4-(2-propynyloxy)-3,5-dimethoxybenzoate

¹H-NMR (CDCl₃) δ: 2.44 (1H, t, J=2.4 Hz), 2.52 (1H, t, J=2.4 Hz), 3.91 (6H, s), 4.81 (2H, d, J=2.4 Hz), 4.92 (2H, d, J=2.4 Hz), 7.33 (2H, s).

To 50 ml of methanol were added 15.5 g of 2-propynyl 4-(2-propynyloxy)-3,5-dimethoxybenzoate and 40 ml of 15% aqueous sodium hydroxide solution and the mixture obtained was stirred at 50° C. for 4 hours. Then, the reaction mixture was added to hydrochloric acid for acidification. Crystals precipitated were collected by filtration and dried to obtain 13.0 g of 4-(2-propynyloxy)-3,5-dimethoxybenzoic acid represented by the formula:

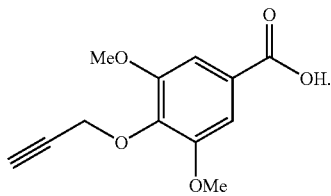

4-(2-Propynyloxy)-3,5-dimethoxybenzoic acid

¹H-NMR (DMSO-d₆) δ: 3.35 (1H, br s), 3.45 (1H, t, J=2.4 Hz), 3.83 (6H, s), 4.70 (2H, d, J=2.4 Hz), 7.24 (2H, s).

To 100 ml of toluene were added 13.0 g of 4-(2-propynyloxy)-3,5-dimethoxybenzoic acid, 9.5 g of thionyl chloride and 50 mg of DMF, and the mixture obtained was heated under reflux for 3 hours. Then, the reaction mixture was concentrated. The solid obtained was washed with hexane to obtain 12.0 g of 4-(2-propynyloxy)-3,5-dimethoxybenzoyl chloride represented by the formula:

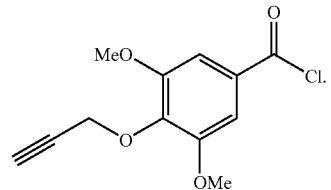

4-(2-Propynyloxy)-3,5-dimethoxybenzoyl chloride

¹H-NMR (CDCl₃) δ: 2.46 (1H, t, J=2.4 Hz), 3.93 (6H, s), 4.87 (2H, d, J=2.4 Hz), 7.38 (2H, s).

REFERENCE PRODUCTION EXAMPLE 2

To 100 ml of DMF were added 10 g of 4-hydroxy-3-methoxybenzoic acid, 15.7 g of propargyl bromide and 18 g of potassium carbonate, and the mixture obtained was stirred at room temperature for 8 hours and at 80° C. for 2 hours. Then, ethyl acetate was added to the reaction mixture and the mixture was filtered through Celite. Water and dilute hydrochloric acid were added to the filtrate in order and it was extracted with ethyl acetate. The organic layer was dried over magnesium sulfate and concentrated under reduced pressure. The crystals obtained were washed with a mix solvent of hexane and MTBE to obtain 13.2 g of 2-propynyl 4-(2-propynyloxy)-3-methoxybenzoate represented by the formula:

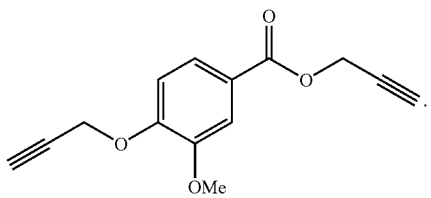

2-Propynyl 4-(2-propynyloxy)-3-methoxybenzoate

¹H-NMR (CDCl₃) δ: 2.52 (1H, t, J=2.5 Hz), 2.55 (1H, t, J=2.4 Hz), 3.93 (3H, s), 4.83 (2H, d, J=2.4 Hz), 4.91 (2H, d, J=2.4 Hz), 7.05 (1H, d, J=8.7 Hz), 7.58 (1H, d, J=1.9 Hz), 7.72 (1H, dd, J=8.5, 1.9 Hz).

To 50 ml of methanol were added 13.2 g of 2-propynyl 4-(2-propynyloxy)-3-methoxybenzoate and 40 ml of 15% aqueous sodium hydroxide solution and the mixture obtained was stirred at room temperature for 8 hours and at 50° C. for 2 hours. Then, the reaction mixture was added to hydrochloric acid for acidification. Crystals precipitated were collected by filtration and dried to obtain 12.0 g of 4-(2-propynyloxy)-3-methoxybenzoic acid represented by the formula:

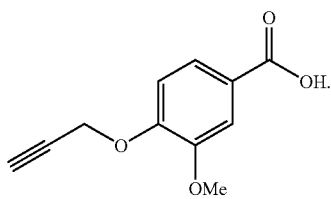

To 100 ml of toluene were added 12.0 g of 4-(2-propynyloxy)-3-methoxybenzoic acid, 9.0 g of thionyl chloride and 50 mg of DMF, and the mixture obtained was heated under reflux for 3 hours. Then, the reaction mixture was concentrated. The solid obtained was washed with hexane to obtain 11.0 g of 4-(2-propynyloxy)-3-methoxybenzoyl chloride represented by the formula.

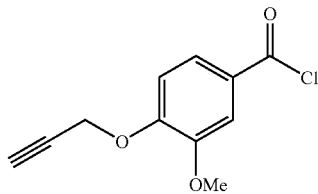

4-(2-Propynyloxy)-3-methoxybenzoyl chloride

¹H-NMR (CDCl₃) δ: 2.59 (1H, t, J=2.4 Hz), 3.94 (3H, s), 4.87 (2H, d, J=2.4 Hz), 7.10 (1H, d, J=8.7 Hz), 7.56 (1H, d, J=2.2 Hz), 7.84 (1H, dd, J=8.7, 2.2 Hz).

REFERENCE PRODUCTION EXAMPLE 3

To 50 ml of DMF were added 5.5 g of 4-hydroxy-3-fluorobenzoic acid, 9.4 g of propargyl bromide and 11 g of potassium carbonate, and the mixture was stirred at room temperature for 8 hours. Then, ethyl acetate was added to the reaction mixture and then, the mixture was filtered through Celite. Water and dilute hydrochloric acid were added to the filtrate in order and it was extracted with ethyl acetate. The organic layer was dried over magnesium sulfate and concentrated under reduced pressure. The residue was subjected to silica gel column chromatography to obtain 10.8 g of 2-propynyl 4-(2-propynyloxy)-3-fluorobenzoate represented by the formula:

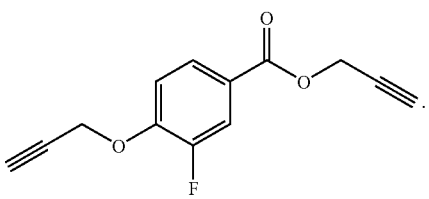

2-Propynyl 4-(2-propynyloxy)-3-fluorobenzoate

¹H-NMR (CDCl₃) δ: 2.50 (1H, t, J=2.5 Hz), 2.56 (1H, t, J=2.4 Hz), 4.82 (2H, d, J=2.4 Hz), 4.89 (2H, d, J=2.4 Hz), 7.13 (1H, t, J=8.3 Hz), 7.78 (1H, dd, J=11.5, 2.1 Hz), 7.82-7.86 (1H, m).

To 50 ml of ethanol were added 10.8 g of 2-propynyl 4-(2-propynyloxy)-3-fluorobenzoate and 30 ml of 15% aqueous sodium hydroxide solution, and the mixture obtained was stirred at room temperature for 2 hours. Then, the reaction mixture was added to hydrochloric acid for acidification. Crystals precipitated were collected by filtration and dried to obtain 8.0 g of 4-(2-propynyloxy)-3-fluorobenzoic acid represented by the formula:

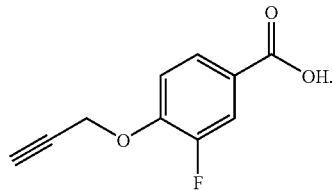

4-(2-Propynyloxy)-3-fluorobenzoic acid

¹H-NMR (DMSO-d₆) δ: 3.21-3.59 (1H, m), 3.68 (1H, t, J=2.3 Hz), 5.01 (2H, d, J=2.2 Hz), 7.34 (1H, t, J=8.5 Hz), 7.71 (1H, dd, J=11.8, 1.9 Hz), 7.77-7.83 (1H, m).

REFERENCE PRODUCTION EXAMPLE 4

(a) To 50 ml of N-methylpyrrolidone were added 10 g of 3,4,5-trifluorobromobenzene and 8.5 g of copper cyanide and the mixture obtained was stirred at 150° C. for 4 hours. Then, aqueous ammonia was added to the reaction mixture and the mixture was extracted with ethyl acetate. The organic layer was dried over magnesium sulfate and concentrated under reduced pressure. The residue was subjected to silica gel column chromatography to obtain 5.0 g of 3,4,5-trifluorobenzonitrile.

To a solution of 5.0 g of 3,4,5-trifluorobenzonitrile and 4.5 g of benzyl alcohol in 25 ml of DMF was added 1.5 g of 60% sodium hydride (oily) at 0° C. The mixture was stirred at room temperature for 4 hours. Then, dilute hydrochloric acid was added to the reaction mixture and the mixture was extracted with ethyl acetate. The organic layer was dried over magnesium sulfate and concentrated under reduced pressure. The residue was subjected to silica gel column chromatography to obtain 7.0 g of 4-benzyloxy-3,5-difluorobenzonitrile represented by the formula:

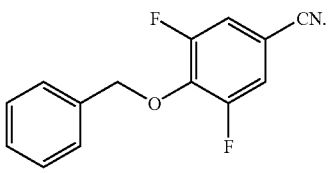

4-Benzyloxy-3,5-difluorobenzonitrile $^1$H-NMR (CDCl$_3$) δ: 5.29 (2H, s), 7.14-7.23 (2H, m), 7.29-7.43 (5H, m).

4-Benzyloxy-3,5-difluorobenzonitrile and 15 ml of concentrated sulfuric acid were added to 100 ml of methanol and the mixture was heated under reflux for 5 days. Then, water was added to the reaction mixture and the mixture was extracted with ethyl acetate. The organic layer was dried over magnesium sulfate and concentrated under reduced pressure. The residue was subjected to silica gel column chromatography to obtain 4.5 g of methyl 3,5-difluoro-4-hydroxybenzoate represented by the formula:

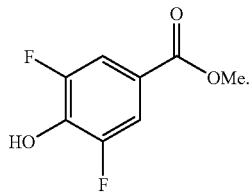

Methyl 3,5-difluoro-4-hydroxybenzoate $^1$H-NMR (CDCl$_3$) δ: 3.91 (3H, s), 6.00 (1H, br s), 7.58-7.67 (2H, m).

To 80 ml of acetonitrile were added 4.5 g of methyl 3,5-difluoro-4-hydroxybenzoate, 3.5 g of propargyl bromide and 9.4 g of cesium carbonate, and the mixture obtained was heated under reflux for 2 hours. The reaction mixture was filtered through Celite. The filtrate was concentrated under reduced pressure. The residue was subjected to silica gel column chromatography to obtain 5.5 g of methyl 3,5-difluoro-4-(2-propynyloxy)benzoate represented by the formula:

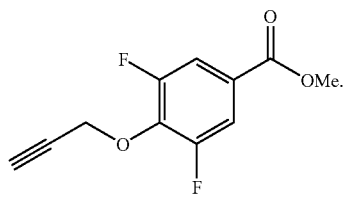

Methyl 3,5-difluoro-4-(2-propynyloxy)benzoate $^1$H-NMR (CDCl$_3$) δ: 2.53 (1H, t, J=2.4 Hz), 3.92 (3H, s), 4.91 (2H, d, J=2.4 Hz), 7.61 (2H, ddd, J=15.1, 7.5, 2.2 Hz).

To 30 ml of ethanol were added 5.5 g of methyl 3,5-difluoro-4-(2-propynyloxy)benzoate and 10 ml of 15% aqueous sodium hydroxide solution and the mixture obtained was stirred at room temperature for 2 hours. Then, the reaction mixture was concentrated under reduced pressure. Hydrochloric acid was added to the residue for acidification and then, solid precipitated was collected by filtration to obtain 5.0 g of 3,5-difluoro-4-(2-propynyloxy)benzoic acid represented by the formula:

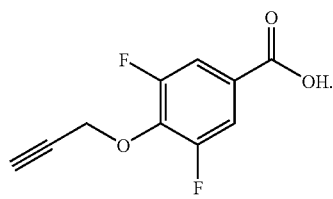

3,5-Difluoro-4-(2-propynyloxy)benzoic acid $^1$H-NMR (CDCl$_3$) δ: 2.54 (1H, t, J=2.2 Hz), 4.94 (2H, d, J=2.2 Hz), 7.65-7.72 (2H, m).

(b) To 50 ml of acetonitrile were added 12 g of propargyl alcohol, 16 g of 3,4,5-trifluorobenzaldehyde and 15 g of potassium carbonate, and the mixture obtained was stirred at room temperature for 1 day. Then, water was added to the reaction mixture and the mixture was extracted with ethyl acetate. The organic layer was washed with dilute hydrochloric acid and brine. The organic layer was dried over magnesium sulfate and concentrated under reduced pressure. The residue was subjected to silica gel column chromatography to obtain 20 g of 3,5-difluoro-4-(2-propynyloxy)benzaldehyde represented by the formula:

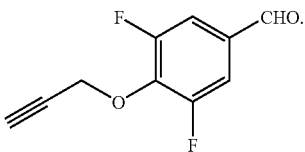

3,5-Difluoro-4-(2-propynyloxy)benzaldehyde $^1$H-NMR (CDCl$_3$) δ: 2.55 (1H, t, J=2.4 Hz), 4.96 (2H, d, J=2.4 Hz), 7.44-7.52 (2H, m), 9.87 (1H, t, J=1.8 Hz).

To 100 ml of chloroform were added 20 g of 3,5-difluoro-4-(2-propynyloxy)benzaldehyde and 25 g of 3-chloroperbenzoic acid and the mixture obtained was stirred at room temperature overnight. Then, aqueous sodium sulfite solution was added to the reaction mixture and extracted with chloroform and ethyl acetate in order. The organic layers were combined, dried over magnesium sulfate and concentrated under reduced pressure to obtain 40 g of 3,5-difluoro-4-(2-propynyloxy)benzoic acid.

(c) To 50 ml of DMF were added 5.0 g of 3,4,5-trifluorobenzoic acid, 4.0 g of propargyl bromide and 4.7 g of potassium carbonate, and the mixture obtained was stirred at room temperature for 30 minutes and then heated with stirring at 80° C. for 1 hour. Then, ethyl acetate was added to the reaction mixture and the mixture was filtered through Celite. Water and dilute hydrochloric acid were added to the filtrate in order and it was extracted with ethyl acetate. The organic layer was dried over magnesium sulfate and concentrated under reduced pressure to obtain 6.0 g of 2-propynyl 3,4,5-trifluorobenzoate represented by the formula:

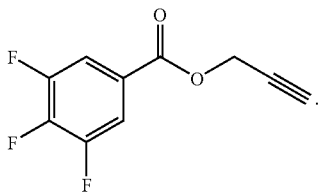

2-Propynyl 3,4,5-trifluorobenzoate $^1$H-NMR (CDCl$_3$) δ: 2.55 (1H, t, J=2.4 Hz), 4.93 (2H, d, J=2.4 Hz), 7.68-7.76 (2H, m).

To a solution of 5.0 g of 2-propynyl 3,4,5-trifluorobenzoate and 1.7 g of propargyl alcohol in 20 ml of DMF was added 1.1 g of 60% sodium hydride (oily) at 0° C. The mixture was stirred at 0° C. for 30 minutes and at room temperature for 1 hour. Then, water was added to the reaction mixture and the mixture was extracted with ethyl acetate. The organic layer was dried over magnesium sulfate and concentrated under reduced pressure. The residue was subjected to silica gel column chromatography to obtain 2.9 g of 2-propynyl 3,5-difluoro-4-(2-propynyloxy)benzoate represented by the formula:

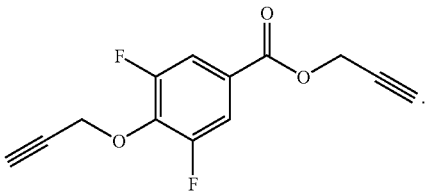

2-Propynyl 3,5-difluoro-4-(2-propynyloxy)benzoate $^1$H-NMR (CDCl$_3$) δ: 2.52 (1H, t, J=2.4 Hz), 2.54 (1H, t, J=2.4 Hz), 4.91 (2H, d, J=2.7 Hz), 4.92 (2H, d, J=2.7 Hz), 7.62-7.68 (2H, m).

To 10 ml of ethanol were added 2.2 g of 2-propynyl 3,5-difluoro-4-(2-propynyloxy)benzoate and 6 ml of 15% aqueous sodium hydroxide solution, and the mixture obtained was stirred at 50° C. for 1 hour. Then, the reaction mixture was concentrated under reduced pressure. Hydrochloric acid was added to the residue for acidification. Crystals precipitated were collected by filtration and dried to obtain 1.8 g of 3,5-difluoro-4-(2-propynyloxy)benzoic acid.

To 17 ml of toluene were added 1.8 g of 3,5-difluoro-4-(2-propynyloxy)benzoic acid, 1 ml of thionyl chloride and 10 mg of DMF, and the mixture was heated under reflux for 4 hours. Then, the reaction mixture was concentrated under reduced pressure to obtain 1.9 g of 3,5-difluoro-4-(2-propynyloxy) benzoyl chloride represented by the formula:

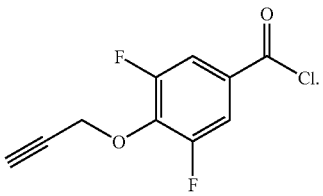

3,5-Difluoro-4-(2-propynyloxy)benzoyl chloride $^1$H-NMR (CDCl$_3$) δ: 2.55 (1H, t, J=2.4 Hz), 4.98 (2H, d, J=2.4 Hz), 7.69-7.76 (2H, m).

REFERENCE PRODUCTION EXAMPLE 5

To 40 ml of acetonitrile were added 7.3 g of 3-fluoro-4-hydroxy-5-methoxybenzaldehyde, 8.8 g of benzyl bromide, 16.8 g of cesium carbonate and 10 ml of DMF, and the mixture obtained was heated under reflux for 10 hours. The reaction mixture was concentrated under reduced pressure. Hydrochloric acid was added to the residue and extracted with ethyl acetate. The organic layer was dried over magnesium sulfate and concentrated under reduced pressure. The residue was subjected to silica gel column chromatography to obtain 7.5 g of 4-benzyloxy-3-fluoro-5-methoxybenzaldehyde represented by the formula:

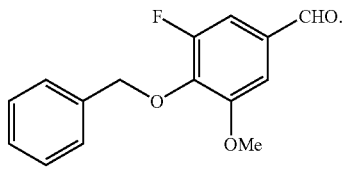

A solution of 7.5 g of 4-benzyloxy-3-fluoro-5-methoxybenzaldehyde in 200 ml of acetone was added dropwise at 15 to 20° C. to a mixture of 200 ml of water and 6.8 g of potassium permanganate. The mixture was stirred at room temperature for 3 days. The reaction mixture was concentrated to about a half amount under reduced pressure. Aqueous sodium hydrogen sulfite solution and dilute hydrochloric acid were added to the concentrate and extracted twice with ethyl acetate. The organic layer was dried over magnesium sulfate and concentrated under reduced pressure to obtain 4-benzyloxy-3-fluoro-5-methoxybenzoic acid.

To 4-benzyloxy-3-fluoro-5-methoxybenzoic acid were added 20 ml of methanol, 20 ml of ethyl acetate and 50 mg of 10% palladium-carbon, and the mixture was stirred at room temperature for 4 hours under hydrogen atmosphere. Then, the reaction mixture was filtered through Celite. The filtrate was concentrated under reduced pressure to obtain 4.5 g of 3-fluoro-4-hydroxy-5-methoxybenzoic acid represented by the formula:

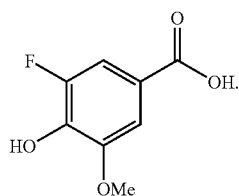

3-Fluoro-4-hydroxy-5-methoxybenzoic acid $^1$H-NMR (DMSO-d$_6$) δ: 3.87 (3H, s), 7.32-7.36 (2H, m)

To 80 ml of DMF were added 4.5 g of 3-fluoro-4-hydroxy-5-methoxybenzoic acid, 7.0 g of propargyl bromide and 9.1 g of potassium carbonate, and the mixture obtained was stirred at room temperature for 2 days. Then, hydrochloric acid was added to the reaction mixture and the mixture was extracted with ethyl acetate. The organic layer was dried over magnesium sulfate and concentrated under reduced pressure. The residue was subjected to silica gel column chromatography to obtain 4.5 g of 2-propynyl 3-fluoro-5-methoxy-4-(2-propynyloxy)benzoate represented by the formula:

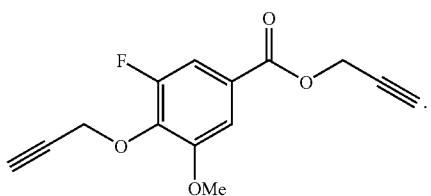

2-Propynyl 3-fluoro-5-methoxy-4-(2-propynyloxy)benzoate $^1$H-NMR (CDCl$_3$) δ: 2.49 (1H, t, J=2.4 Hz), 2.54 (1H, t, J=2.4 Hz), 3.94 (3H, s), 4.87 (2H, d, J=2.4 Hz), 4.91 (2H, d, J=2.4 Hz), 7.43 (1H, dd, J=1.8, 1.8 Hz), 7.48 (1H, dd, J=10.4, 1.8 Hz).

To 40 ml of methanol were added 4.5 g of 2-propynyl 3-fluoro-5-methoxy-4-(2-propynyloxy)benzoate and 20 ml of 15% aqueous sodium hydroxide solution, and the mixture obtained was stirred at room temperature for 8 hours. Then, the reaction mixture was concentrated. Hydrochloric acid was added to the residue for acidification. Solids precipitated were collected by filtration and dried to obtain 3.7 g of 3-fluoro-5-methoxy-4-(2-propynyloxy)benzoic acid represented by the formula:

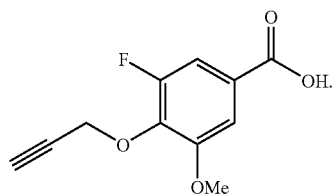

3-Fluoro-5-methoxy-4-(2-propynyloxy)benzoic acid $^1$H-NMR (CDCl$_3$) δ: 2.50 (1H, t, J=2.4 Hz), 3.95 (3H, s), 4.89 (2H, d, J=2.4 Hz), 7.46-7.57 (2H, m).

Then, Formulation Examples are shown. All the parts are parts by weight.

FORMULATION EXAMPLE 1

A wettable powder for each compound of the present invention is obtained by thoroughly pulverizing and mixing 50 parts of each of the compounds 1 to 48 of the present invention, 3 parts of calcium lignin sulfonate, 2 parts of magnesium lauryl sulfonate and 45 parts of synthetic hydrous silicon oxide.

FORMULATION EXAMPLE 2

After mixing 20 parts of each of the compounds 1 to 48 of the present invention and 1.5 parts of sorbitan trioleate with 28.5 parts of aqueous solution containing 2 parts of polyvinyl alcohol, the mixture is finely pulverized by a wet pulverization method. Then, 40 parts of aqueous solution containing 0.05 part of xanthan gum and 0.1 part of aluminum magnesium silicate are added thereto. Further, 10 parts of propylene glycol is added thereto and the mixture was mixed to obtain a flowable preparation for each compound of the present invention.

FORMULATION EXAMPLE 3

A dust for each compound of the present invention is obtained by thoroughly pulverizing and mixing 2 parts of each of the compounds 1 to 48 of the present invention, 88 parts of kaolin clay and 10 parts of talc.

FORMULATION EXAMPLE 4

An emulsion for each compound of the present invention is obtained by thoroughly mixing 5 parts of each of the compounds 1 to 48 of the present invention, 14 parts of polyoxyethylene styrylphenyl ether, 6 parts of calcium dodecylbenzene sulfonate and 75 parts of xylene.

FORMULATION EXAMPLE 5

A granule for each compound of the present invention is obtained by thoroughly pulverizing and mixing 2 parts of each of the compounds 1 to 48 of the present invention, 1 part of synthetic hydrous silicon oxide, 2 parts of calcium lignin sulfonate, 30 parts of bentonite and 65 parts of kaolin clay, adding water, thoroughly kneading the mixture, granulating and drying.

FORMULATION EXAMPLE 6

A flowable preparation for each compound of the present invention is obtained by mixing 10 parts of each of the compounds 1 to 48 of the present invention, 35 parts of white carbon containing 50 parts of ammonium polyoxyethylene alkyl ether sulfate and 55 parts of water and thoroughly pulverizing the mixture by a wet pulverization method.

Next, the following Test Examples will demonstrate that the compounds of the present invention are useful for controlling plant diseases.

In Test Examples, the controlling activity was evaluated by visually observing the areas of lesions on plants tested and comparing the area of the lesion of a plant treated with the compound of the present invention with the area of the lesion of a plant without the treatment.

TEST EXAMPLE 1

Sandy loam was packed in plastic pots and seeds of tomato (variety: Patio) were sowed and grown in a greenhouse for 20 days. A flowable preparation for each of the compounds 1, 2, 3, 4, 5, 6, 7, 9, 10, 11, 12, 13, 14, 15, 16, 18, 20, 21, 22, 24, 25, 26, 27, 29, 32, 34, 35, 36, 40, 44, 45, 46, 50, 55 and 56 of the present invention was prepared according to Formulation Example 6, and then the preparation was diluted with water so that the concentration of the compound of the present invention was 500 ppm to prepare a test solution. The test solution was sprayed on the leaves and stems so that the solution thoroughly adhered to the leaf surfaces of the above-mentioned tomato seedling. After air-drying the test solution on the leaf surfaces, an aqueous suspension of zoosporangia of Phytophthora infestans (about 30,000/ml) was sprayed on the tomato seedling (at a proportion of about 2 ml per one seedling). The tomato seedling was cultivated under conditions of 23° C. and a relative humidity of 90% or more for one day, transferred to a greenhouse at 24° C. during daytime and 20° C. at night, and then cultivated for 4 days, followed by examining the lesion area of Phytophthora infestans of the tomato seedling.

The lesion areas in the seedlings treated with the compounds 1, 2, 3, 4, 5, 6, 7, 9, 10, 11, 12, 13, 14, 15, 16, 18, 20, 21, 22, 24, 25, 26, 27, 29, 32, 34, 35, 36, 40, 44, 45, 46, 50, 55 and 56 of the present invention were 30% or less as compared with the lesion areas in seedlings without the treatment.

TEST EXAMPLE 2

Sandy loam was packed in plastic pots and the seeds of tomato (variety: Patio) were sowed and grown in a greenhouse for 20 days. A flowable preparation for each of the compounds 1, 2, 3, 5, 7, 9, 10, 11, 12, 13, 14, 15, 16, 18, 19, 20, 22, 23, 25, 26, 30, 31, 33, 34, 35, 37, 39, 40, 41, 42, 43, 44, 45 and 46 of the present invention was prepared according to Formulation Example 6, and the preparation was diluted with water so that the concentration of the compound of the present invention was 200 ppm to prepare a test solution. The test solution was sprayed on the leaves and stems so that the test solution thoroughly adhered to the leaf surfaces of the above-mentioned tomato seedling. After air-drying the test solution on the leaf surfaces, an aqueous suspension of zoosporangia of Phytophthora infestans (about 30,000/ml) was sprayed on the tomato seedling (at a proportion of about 2 ml per one plant). The tomato seedling was cultivated under conditions of 23° C. and a relative humidity of 90% or more for one day, transferred to a greenhouse at 24° C. during daytime and 20° C. at night, and cultivated for 4 days, followed by examining the lesion area of Phytophthora infestans in the tomato seedling.

The lesion areas in the seedlings treated with the compounds 1, 2, 3, 5, 7, 9, 10, 11, 12, 13, 14, 15, 16, 18, 19, 20, 22, 23, 25, 26, 30, 31, 33, 34, 35, 37, 39, 40, 41, 42, 43, 44, 45 and 46 of the present invention were 30% or less as compared with the lesion areas in seedlings without treatment.

TEST EXAMPLE 3

Sandy loam was packed in plastic pots with a volume of 160 ml and seeds of tomato (variety: Patio) were sowed and grown in a greenhouse for 13 days. A flowable preparation for each of the compounds 9, 10, 11, 13, 14, 15, 16, 17, 18, 19, 20, 21, 22, 23, 25, 30, 32, 34, 35, 36, 38, 39, 41, 42, 43, 44, 45, 46, 48 and 49 of the present invention was prepared according to Formulation Example 6, and the preparation was diluted with water so that the concentration of the compound of the present invention was 200 ppm to prepare a test solution. The test solution was applied to the plant bottom of the above-mentioned tomato seedling by irrigation treatment at a rate of 20 ml per one pot. The tomato seedling was transferred to a greenhouse at 24° C. during daytime and 20° C. at night and cultivated for 7 days. Then, an aqueous suspension of zoosporangia of Phytophthora infestans (about 30,000/ml) was sprayed on the tomato seedling (at a proportion of about 2 ml per one plant). The tomato seedling was cultivated under conditions of 23° C. and a relative humidity of 90% or more for one day, transferred to a greenhouse at 24° C. during daytime and 20° C. at night and cultivated for 4 days, followed by examining the lesion area of Phytophthora infestans of the tomato seedling.

The lesion areas in the seedlings treated with the compounds 9, 10, 11, 13, 14, 15, 16, 17, 18, 19, 20, 21, 22, 23, 25, 30, 32, 34, 35, 36, 38, 39, 41, 42, 43, 44, 45, 46, 48 and 49 of the present invention were 30% or less as compared with the lesion areas in seedlings without treatment.

INDUSTRIAL APPLICABILITY

Since the compound of the present invention is very effective for controlling plant diseases, it is useful as an effective ingredient of a composition for controlling plant diseases.

The invention claimed is:

1. An amide compound represented by the formula (1)

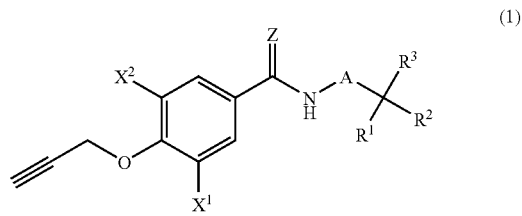

wherein $X^1$ represents a fluorine atom or a methoxy group,
$X^2$ represents a hydrogen atom, a fluorine atom or a methoxy group,
Z represents an oxygen atom or a sulfur atom,
A represents a single bond or a methylene group,
$R^1$ and $R^2$ represent independently a C1 to C4 alkyl group, and
$R^3$ represents a hydrogen atom, a C1 to C4 alkyl group, a C2 to C4 alkenyl group, a C2 to C4 alkynyl group, a cyano group, a carboxyl group, or a (C1 to C3 alkoxy) carbonyl group.

2. The amide compound according to claim 1, wherein, in the formula (1), Z is an oxygen atom.

3. The amide compound according to claim 1, wherein, in the formula (1), $X^1$ is a fluorine atom and $X^2$ is a hydrogen atom; or $X^1$ is a fluorine atom and $X^2$ is a fluorine atom; or $X^1$ is a methoxy group and $X^2$ is a hydrogen atom; or $X^1$ is a methoxy group and $X^2$ is a methoxy group.

4. The amide compound according to claim 1, wherein, in the formula (1), $X^1$ is a methoxy group and $X^2$ is a methoxy group.

5. The amide compound according to claim 1, wherein, in the formula (1), $X^1$ is a methoxy group and $X^2$ is a hydrogen atom.

6. The amide compound according to claim 1, wherein, in the formula (1), A is a single bond.

7. The amide compound according to claim 1, wherein, in the formula (1), $R^1$ is a methyl group or an ethyl group and $R^2$ is a methyl group, an ethyl group, a 1-methylethyl group, a 1,1-dimethylethyl group or a 1-methylpropyl group.

8. The amide compound according to claim 1, wherein, in the formula (1), $R^3$ is a hydrogen atom or a methyl group.

9. The amide compound according to claim 1, wherein, in the formula (1), $X^1$ is a fluorine atom and $X^2$ is a hydrogen atom.

10. The amide compound according to claim 1, wherein, in the formula (1), $X^1$ is a fluorine atom and $X^2$ is a fluorine atom.

11. A composition for controlling plant diseases which comprises the amide compound according to claim 1 as an effective ingredient and an inactive carrier.

12. A method for controlling plant diseases which comprises a step of treating a plant or soil growing the plant with an effective amount of the amide compound according to claim 1.

* * * * *